(12) United States Patent  
Carpino

(10) Patent No.: US 6,337,332 B1  
(45) Date of Patent: Jan. 8, 2002

(54) NEUROPEPTIDE Y RECEPTOR ANTAGONISTS

(75) Inventor: Philip A. Carpino, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/382,418

(22) Filed: Aug. 24, 1999

Related U.S. Application Data

(60) Provisional application No. 60/100,749, filed on Sep. 17, 1998.

(51) Int. Cl.[7] ....................... A01N 43/54; A61K 31/505; C07D 239/70; C07D 417/00; C07D 239/72
(52) U.S. Cl. ....................... 514/259; 514/260; 544/283; 544/284; 544/290; 544/293
(58) Field of Search ................................. 514/259, 260; 544/283, 284, 290, 293

(56) References Cited

U.S. PATENT DOCUMENTS 4,294,851 A * 10/1981 Metz et al. .................. 514/546
4,668,682 A *  5/1987 Sekiya et al. ............... 514/259
5,747,497 A *  5/1998 Bereznak et al. ........... 514/259

FOREIGN PATENT DOCUMENTS

EP  WO97/24369  10/1997
WO  WO97/09308   3/1997

OTHER PUBLICATIONS

Abe et al., "Effects of MCI–176, A New Quinazolone Calcium Antagonists, . . . ", Biochem. Pharmacol., (1991), vol. 41(3), pp. 445–451.*

* cited by examiner

Primary Examiner—Mukund J. Shah
Assistant Examiner—Tamthom N. Truong
(74) Attorney, Agent, or Firm—Peter C. Richardson; Gregg C. Benson; Gabriel L. Kleiman

(57) ABSTRACT

Compounds of the structures

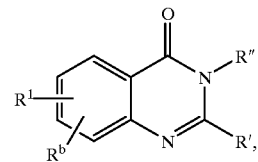

I

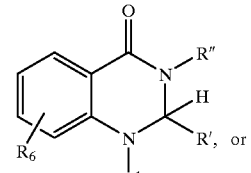

II

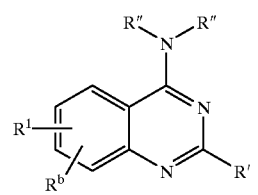

V are useful for treating conditions related to an excess of neuropeptide Y including obesity and circulatory disorders.

4 Claims, No Drawings

NEUROPEPTIDE Y RECEPTOR ANTAGONISTS

This application is filed claiming priority from co-pending Provisional Application No. 60/100,749 filed Sep. 17, 1998.

A notice of Allowance is courteously solicited.

BACKGROUND OF INVENTION

1. Field of the Invention

This invention relates to the use of certain substituted heterocyclic compounds which selectively bind to mammalian neuropeptide receptors. It further relates to the use of such compounds and compositions in treating conditions related to an excess of neuropeptide Y such as feeding disorders and certain cardiovascular diseases.

2. Description of the Related Art

Neuropeptide Y, a peptide first isolated in 1982, is widely distributed in the central and peripheral neurons and is responsible for a multitude of biological effects in the brain and the periphery. Various animal studies have shown that activation of neuropeptide Y1 receptors is related to vasoconstriction, Wahlestedt et al. *Regul. Peptides*, 13: 307–318 (1986), McCauley and Westfall, *J. Pharmacol. Exp. Ther.* 261:863–868 (1992), and Grundemar et al., *Br. J. Pharmacol.* 105:45–50 (1992); and to stimulation of consummatory behavior, Flood and Morley, *Peptides*, 10:963–966 (1989), Leibowitz and Alexander, *Peptides*, 12:1251–1260 (1991), and Stanley et al. *Peptides*,. 13:581–587 (1992).

Grundemar and Hakanson. *TIPS*, May 1994 [Vol. 15], 153–159, state that, in animals, neuropeptide Y is a powerful stimulus of food intake, and an inducer of vasoconstriction leading to hypertension. They further point out that low levels of neuropeptide Y (NPY) are associated with loss of appetite. These reports clearly indicate that compounds that inhibit the activity of this protein will reduce hypertension and appetite in animals.

EP0759441 and U.S. Pat. No. 5,576,337 report that physiological disorders related to neuropeptide Y include:

disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and sugery in the gastrointestinal tract;

cerebral diseases and diseases related to the central nervous system, such as cerebral infarction, neurodegeneration, epilepsy, stroke, and conditions related to stroke, cerebral vasospasm and hemmorrhage, depression, anxiety, schizophrenia, and dementia;

conditions related to pain or nociception;

diseases related to abnormal gastrointenstinal motility and secretion, such as different forms of ileus, urinary incontinence, and Crohn's disease;

abnormal drink and food intake disorders, such as anorexia and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

WO 96/14307 describes substituted benzylamine derivatives which selectively bind to human neuropeptide Y1 receptors.

The synthesis of certain 4-aminopyrrole (3,2-d) pyridines is described in *Pharm. Chem J.* 22,185 (1988); 8, 14 (1974); and 7, 19 (1973). These compounds were reported to have antibacterial and antitumor activity.

SUMMARY OF THE INVENTION

This invention provides a compound of the formula:

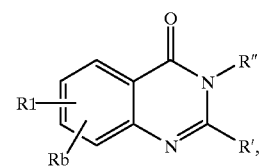

I

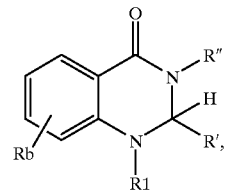

II

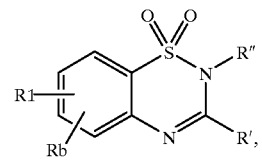

III

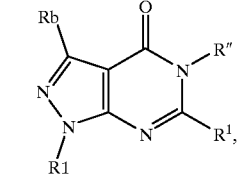

IV

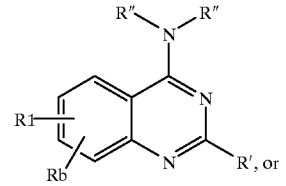

V

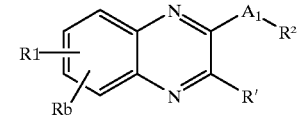

VI wherein:

R' is —A—A$^1$—(CH$_2$)$_p$—R

R" is (CH$_2$)$_q$—D—(CH$_2$)$_s$—CX$^1$Y$^1$—R$^2$

R$^b$ is hydrogen, C$_1$–C$_6$ alkyl, C$_1$–C$_6$ alkoxy, C$_2$–C$_6$ alkanoyl, trifluoromethyl, hydroxy, or halo;

$R^1$ is hydrogen, $C_1$–$C_6$ alkyl, or —$(CH_2)_v$—$R^{1a}$;

where v is 1 to 12, and $R^{1a}$ is phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl, any one of which phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl groups may be substituted with one or more moieties selected from the groups consisting of $C_1$–$C_6$ alkyl, halo, trifluoromethyl, benzyl, phenyl, di($C_{1-C6}$ alkyl)amino, $C_1$–$C_6$ alkylamino, $C_2$–$C_6$ alkanoyl, $C_2$–$C_6$ alkanoyloxy, and $C_3$–$C_8$ cycloalkyl, said phenyl, benzyl, or $C_3$–$C_8$ cycloalkyl, being optionally substituted with one, two or three moieties independently selected from the group consisting of $C_1$–$C_6$ alkyl, halo, or $C_1$–$C_6$ alkoxy;

or $R^{1a}$ may be substituted with —$(CH_2)_w R^{1b}$, where w is 1 to 12 and $R^{1b}$ is piperidinyl, pyrimidyl, pyrrolidinyl, $C_1$–$C_6$ alkoxy, $C_1$–$C_6$ alkylthio, di[di($C_1$–$C_6$ alkyl)amino($C_1$–$C_6$ alkylenyl)amino, phenyl, $C_3$–$C_8$ cycloalkyl, pyrrolidinyl, and acetamido;

said phenyl, or $C_3$–$C_8$ cycloalkyl, being optionally substituted with one, two, or three moieties independently selected from the group consisting of $C_1$–$C_6$ alkyl, halo, or $C_1$–$C_6$ alkoxy;

A is a bond, —$(CH_2)_m$ or —C(O)—;

$A^1$ is a bond, —$NR^a$—, —O—, —$(CH_2)_m$—, or $S(O)_n$—;

q is 0 to 6;

p is 0 to 6;

n is 0, 1, or 2;

m is 0 to 6;

s is 0 to 6;

$R^a$ is hydrogen, $C_1$–$C_6$ alkyl, or $C_2$–$C_6$ alkanoyl;

D is a bond, $C_2$–$C_4$ alkenylenyl, or —C(X)(Y)—, where one of X and Y is hydroxy and the other is hydrogen, or both X and Y are hydrogen, or X and Y combine to form =O, or =$NOR^c$;

$R^c$ is hydrogen, benzyl, acetyl, benzoyl, or $C_1$–$C_6$ alkyl;

one of $X^1$ and $y^1$ is hydroxy and the other is hydrogen, or one of $X^1$ and $y^1$ is hydroxy and the other is hydrogen, or both $X^1$ and $y1$ are hydrogen, or $X^1$ and $Y^1$ combine to form =O, or =$NOR^d$;

$R^d$ is hydrogen or $C_1$–$C_6$ alkyl;

$R^2$ is hydroxy, $C_1$–$C_6$ alkyl, $C_1$–$C_6$ alkoxy, phenoxy, or a group of the formula

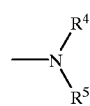

wherein $R^4$ and $R^5$ are independently hydrogen, $C_1$–$C_6$ alkyl, phenyl, or phenyl($C_1$–$C_6$ alkylenyl)-, or $R^2$ is a heterocyclic ring selected from the group consisting of hexamethyleneiminyl, piperazinyl, heptamethyleneiminyl, imidazolinyl, piperdinyl, 2-tryptolinyl, pyrrolidinyl, quinuclidinyl, or morpholinyl;

any one of which hexamethyleneiminyl, piperazinyl, heptamethyleneiminyl, imidazolinyl, piperidinyl, 2-tryptolinyl, pyrrolidinyl, quinuclidinyl, or morpholinyl groups may be substituted with one or more moieties selected from the group consisting of $C_1$–$C_6$ alkyl, halo, trifluoromethyl, benzyl, phenyl, di($C_1$–$C_6$ alkyl)amino, do($C_1$–$C_6$ alkyl)amino($C_1$–$C_6$ alkylenyl)-, $C_1$–$C_6$ alkylamino($C_1$–$C_6$ alkylenyl)-, $C_2$–$C_6$ alkanoyl, carboxamido, 2-aminoacetyl, $C_2$–$C_6$ alkanoyloxy, $C_1$–$C_6$ alkoxycarbonyl-, $C_1$–$C_6$ alkylamino, $C_3$–$C_8$ cycloalkyl, piperidinyl, pyrrolidinyl, pyrimidyl, phenyl($C_1$–$C_6$ alkylenyl)-, phenoxy($C_1$–$C_6$ alkylenyl)-, piperidinyl($C_1$–$C_6$ alkylenyl)-, pyrrolidinyl($C_1$–$C_6$ alkylenyl)-, pyrimidyl($C_1$–$C_6$ alkylenyl)-, $C_1$–$C_6$ alkoxy, $C_1$–$C_6$ alkylthio, di[di($C_1$–$C_6$ alkyl)amino ($C_1$–$C_6$ alkylenyl)]amino, di($C_1$–$C_6$ alkyl)amino ($C_1$–$C_6$ alkylenyl)amino, and acetamido, any one of said benzyl, phenyl, piperidinyl, $C_3$–$C_8$ cycloalkyl, phenyl($C_1$–$C_6$ alkylenyl)-, phenoxy($C_1$–$C_6$ alkylenyl)-, pyrrolidinyl, piperidinyl($C_1$–$C_6$ alkylenyl)-, pyrrolidinyl($C_1$–$C_6$ alkylenyl)-, pyrrolidinyl($C_1$–$C_6$ alkylenyl)-, pyrimidyl($C_1$–$C_6$ alkylenyl)-, or pyrimidyl group may be substituted with one or more moieties selected from the group consisting of $C_1$–$C_6$ alkyl, halo, trifluoromethyl, acetamido, $C_2$–$C_6$ alkanoyl, $C_2$–$C_7$ alkanoyloxy, and $C_1$–$C_6$ alkoxy, or the nitrogen on said piperidinyl, pyrrolidinyl, piperidinyl($C_1$–$C_6$ alkylenyl)-, pyrrolidinyl($C_1$–$C_6$ alkylenyl)-, or pyrimidyl may be substituted with an amino-protecting group, or $R^2$ is a group of the formula

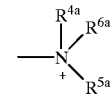

where $R^{4a}$, $R^{5a}$, and $R^{6a}$ are independently hydrogen, $C_1$–$C_6$ alkyl, trifluoromethyl, or $C_1$–$C_6$ alkoxy, or $R^{4a}$ is hydrogen, $C_1$–$C_6$ alkyl, trifluoromethyl, or $C_1$–$C_6$ alkoxy and $R^{5a}$ and $R^{6a}$ combine to form, together with the nitrogen to which they are attached, pyrrolidinyl, piperidinyl, hexamethyleneiminyl, or heptamethyleneiminyl, or, $R^{4a}$ is oxygen, and $R^{5a}$ and $R^{6a}$ combine to form, together with the nitrogen to which they are attached, pyrrolidinyl, piperidinyl, hexamethyleneiminyl, or heptamethyleneiminyl;

R is phenyl, naphthyl, dihydronaphthyl, tetrahydronaphthyl, $C_3$–$C_8$ cycloalkyl, pyrazinyl, allyl, thiazolyl, furyl, pyrimidyl, pyridinyl, quinolinyl, isoquinolinyl, oxazolyl, pyradizinyl, imidazolyl, triazolyl, tetrazolyl, hexamethyleneiminyl, heptamethyleneiminyl, piperidinyl, pyrrolidinyl, quinuclidinyl, or morpholinyl, any one of said phenyl, naphthyl, dihydronaphthyl, tetrahydronaphthyl, $C_3$–$C_8$ cycloalkyl, pyrazinyl, thiazolyl, furyl, pyrimidyl, pyridinyl, quinolinyl, isoquinolinyl, oxazolyl, pyridazinyl, imidazolyl, triazolyl, tetrazolyl, hexamethyleneiminyl, heptamethyleneiminyl, piperidinyl, pyrrolidinyl, quinuclidinyl, or morpholinyl groups may be substituted with one or more moieties selected from the group consisting of $C_1$–$C_{12}$ alkyl, $C_2$–$C_{10}$ alkenyl, $C_2$–$C_{10}$ alkynyl, halo, trifluoromethyl, carboxamido, cyano, benzyl, phenyl, di($C_1$–$C_{12}$ alkyl)amino, $C_2$–$C_6$ alkanoyl, $C_2$–$C_6$ alkanoyloxy, $C_1$–$C_6$ alkylamino, oxazolyl, dihydrooxazolyl, piperidinyl($C_1$–$C_{12}$ alkoxy)-, piperidinyl($C_1$–$C_{12}$ alkoxy)($C_1$–$C_{12}$ alkoxy) ($C_1$–$C_6$) alkylenyl)-, piperidinyl($C_1$–$C_{12}$ alkylenyl)-, phenyl($C_1$–$C_{12}$ alkoxy)-, phenyl($C_2$–$C_{12}$) alkylenyl)-, $C_3$–$C_8$ cycloalkyl, piperidinyl, pyrimidyl, $C_1$–$C_6$ alkoxy, $C_1$–$C_6$ alkylthio, a group of the formula $R^xR^yN$-G-L-($C_0$–$C_6$ alkylenyl)-, and acetamido, where $R^x$ and $R^y$ are independently hydrogen $C_1$–$C_6$ alkyl, phenyl, benzyl, piperidinyl, pyrrolidinyl, hexamethyleneiminyl, heptamethyleneiminyl, heptamethyleneiminyl, azetidinyl, which may be attached to G at any appropriate place on the ring, G is $C_1$–$C_{12}$ alkylenyl, $C_2$–$C_{12}$ alkenylenyl, or $C_2$–$C_{12}$ alkynylenyl, and L is a bond, —O—, —S—, —S(O)—, —S(O)$_2$—, or —NH—;

with the proviso that when, $A^1$ is —$NR^a$—, —O—, or —S(O)$_n$—, and A is —$CH_2$—, $R^1$ is not hydrogen; or a pharmaceutically acceptable salt or solvate thereof.

In another aspect this invention provides a compound selected from formula I or III wherein $R^1$ is hydrogen, or methyl or OMe and $R^{1a}$ is piperidinyl, pyrrolidinyl, piperazinyl, or quinuclidinyl, or a pharmaceutically acceptable salt or solvate thereof.

In another aspect this invention provides a compound selected from formula I, II or III wherein $R^{1a}$ is piperidin-3-yl, piperidin-2-yl, pyrrolidin-3-yl, or pyrrolidin-2-yl, piperidin-1-yl, piperidin-4-yl, pyrroldin-1-yl, or pyrrolidin-4-yl, phenyl, or a pharmaceutically acceptable salt or solvate thereof.

In another aspect the invention provides a compound of formula I, II or III wherein $A^1$ is a bond or —O—; or a pharmaceutically acceptable salt or solvate thereof.

In another aspect the invention provides a compound selected from formula I, II or III wherein —($CH_2$)$_q$—D—($CH_2$)$_s$— is a bond, methylene, ethylene, or —C(O)—; or a pharmaceutically acceptable salt or solvate thereof.

In another aspect this invention provides a compound of formulae I–VI wherein both $X^1$ and $Y^1$ are hydrogen; or a pharmaceutically acceptable salt or solvate thereof.

In another aspect this invention provides a compound of formulae I–VI wherein $R^2$ is a piperidinyl group substituted with amino, di($C_1$–$C_6$ alkyl)amino, $C_1$–$C_6$ alkylamino, or piperidinyl, or $R^2$ is a pyrroldinyl group substituted with amino, di($C_1$–$C_6$) alkyl)amino, $C_1$–$C_6$ alkylamino, or pyrroldinyl, or $R^2$ is a piperazinyl group substituted with phenyl or cyclohexyl; or a pharmaceutically acceptable salt or solvate thereof.

In another aspect this invention provides a compound of formulae I–VI wherein —A—$A^1$—($CH_2$)$_p$— is —$CH_2$—O—, —$CH_2$—NH—, or —$CH_2$—S—; or a pharmaceutically acceptable salt or solvate thereof.

In another aspect this invention provides a compound of formulae I–VI wherein R is naphthyl, phenyl, piperidinyl, pyrrolidinyl, or cyclohexyl; or a pharmaceutically acceptable salt or solvate thereof.

In another aspect this invention provides a compound of formulae I–VI wherein R is phenyl optionally independently substituted at the 4-position and at the 2-position with halo; or a pharmaceutically acceptable salt or solvate thereof.

In another aspect this invention provides a compound of formula I wherein:

$R^1$ is H, Me, O-alkyl, —O($CH_2$)$_v$$R^{1a}$, amino, alkylamino, dialkylamino where the alkyl group is optionally substituted with halo, or OMe;

$R^b$ is H, halo or alkoxy;

$R^{1a}$ is piperidine or pyrrolidine;

$R^1$ is $CH_2OR$, $CH_2CH_2R$, CH=CHR, or $CH_2SR$; R is pyridine, phenyl, naphthalene, thiadiazole, optionally substituted with halo, alkyl, alkoxy, $CF_3$, $OCF_3$, alkylamino, or dialkylamino;

R" is ($CH_2$)$_q$$R^2$;

$R^2$ is piperidine, pyrolidine, morpholine, or piperazine optionally substituted with ($CH_2$)$_v$$R^{1a}$, or ($CH_2$)$_v$A' ($CH_2$)$_v$$R^{1a}$;

A' is N, or O; and $R^{1a}$ is phenyl, pyridine, imidazole, pyrrole, piperidine, or pyrrolidine; wherein the phenyl, pyridine are optionally substituted with halo, O-Alkyl, alkyl, nitro, or cyano wherein the alkyl are optionally substituted with halo;

In another aspect this invention provides a compound of formulae I–VI wherein:

$R^1$ is OMe, $OCHF_2$, OEt, O—iPr, or O—$_c$Pr;

Rb is H, or halo;

$R^1$ is $CH_2OR$, or CH=CHR;

R is pyridine, phenyl, or naphthalene optionally substituted with halo, $CF_3$, $OCF_3$, amino, alkylamino, or dialkylamino;

R" is ($CH_2$)$_q$$R^2$;

$R^2$ is piperidine, or piperazine optionally substituted with ($CH_2$)$_v$$R^{1a}$; and $R^1$ a is phenyl, pyridine, piperidine, or pyrrolidine; and the phenyl and pyridine optionally substituted with halo, alkoxy, or alkyl.

In another aspect this invention provides a compound of formula I wherein:

$R^1$ is OMe;

$R^b$ is H;

R is 4-Cl—Ph, 3-Cl—Ph, 2-Cl—Ph, 4-F—Ph, 4-$CF_3$—Ph, or 4-OMePh;

R' is $CH_2OR$;

$R^2$ is piperidine, or piperazine optionally substituted with ($CH_2$)$_v$$R^{1a}$; and $R^{1a}$ is pyridine, piperidine, pyrolidine, or phenyl optionally substituted with halo, or alkoxy.

In another aspect this invention provides a compound of formula I wherein:

R is 4-Cl—Ph;

q is 3;

v is 3;

$R^2$ is piperidine; and $R^{1a}$ is piperidine.

In another aspect this invention provides a compound of formula I which is 2-(4-chloro-phenoxymethyl)-8-methoxy-3-{3-[1-(3-piperidin-1-yl-propyl)-piperidin-4-yl]-propyl}-3H-quinazolin-4-one.

In another aspect this invention provides a compound of formula I, II or III wherein:

R is 4-Cl—Ph;

q is 3;

v is 2;

$R^2$ is piperazine; and $R^{1a}$ is phenyl.

In another aspect this invention provides a compound of formula I, II or III which is 2-(4-chloro-phenoxymethyl)-8-methoxy-3-[3-(4-phenethyl-piperazin-1-yl)-propyl]-3H-quinazolin-4-one.

In another aspect this invention provides a compound of formula I wherein:

$R^1$ is 4-Cl—Ph, 3-Cl—Ph, 2-Cl—Ph, 4-F—Ph, 4-$CF_3$-Ph, or 4-OMePh;

R is CH=CH, or CH$_2$CH$_2$;

R$^2$ is piperidine, piperazine optionally substituted with (CH2)$_v$R$^{1a}$; and R$^{1a}$ is pyridine, piperidine, pyrolidine, phenyl, or pyridyl; wherein said phenyl and pyridyl are optionally substituted with halo, alkoxy, or alkyl.

In another aspect this invention provides a compound of formula I wherein:

R' is 4-Cl—Ph;

R is 2, CH=CH;

q is 3;

v is 3; and

R$^{1a}$ is piperidine;

In another aspect this invention provides the compound of formula I which is 2-[2-(4-chloro-phenyl)-vinyl]-8-methoxy-3-{3-[1-(3-piperidin-1-yl-propyl)-piperidin-4-yl]-propyl}-3H-quinazolin-4-one.

In another aspect this invention provides a compound of formula VI wherein:

R$^1$ is H, alkyl, O-Alkyl, —O(CH$_2$)$_v$R$^{1a}$ where the alkyl is optionally substituted with halo, cyano;

R$^b$ is H, halo, alkoxy;

R$^{1a}$ is piperidine, pyrrolidine;

R' is CH$_2$OR, CH$_2$CH$_2$R, CH=CHR, or CH$_2$SR;

R is pyridine, phenyl, or naphthalene each optionally substituted with halo, alkyl, alkoxy, CF$_3$, or CF$_3$O;

A1 is NH, O, S, or CH$_2$;

R" is (CH$_2$)$_q$R$^2$; and q is 0–4;

R$^2$ is piperidine, pyrolidine, morpholine, or piperazine each optionally substituted with (CH$_2$)$_v$R$^{1a}$, or (CH2)$_v$A'(CH2)$_v$R$^{1a}$;

A' is N, O; and

R$^{1a}$ is phenyl, pyridine, imidazole, pyrrole, piperidine, or pyrrolidine; wherein the phenyl and pyridine are optionally substituted with halo, alkoxyl, alkyl, CF$_3$, CF$_3$O, nitro, or cyano.

In another aspect this invention provides a compound of formula VI wherein:

R$^1$ is H, O-alkyl, halo, —O(CH$_2$)$_v$R1a wherein alkyl is optionally substituted with halo;

R$^b$ is H, O-alkyl, or halo where the alkyl is optionally substituted with halo;

A1 is NH;

R' is CH=CHR;

R is phenyl, pyridyl, napthalene optionally substituted with halo, alkoxy;

R" is (CH$_2$)$_q$R$^2$;

R$^2$ is piperidine optionally substituted with (CH$_2$)$_v$R1a;

R$^{1a}$ is phenyl, pyridine, piperidine, or pyrrolidine; wherein the phenyl and pyridine are optionally substituted with halo, alkoxy, or alkyl.

In another aspect this invention provides a compound of formula VI wherein:

R$^1$ is O-alkyl, Cl, F, or CF$_3$O;

R$^b$ is O-alkyl, Cl, F, or CF$_3$O;

R is phenyl, or pyridyl each optionally substituted with halo;

R" is (CH$_2$)$_q$R$^2$;

R$^2$ is piperidine, or pyrrolidine each optionally substituted with (CH2)$_v$R1a;

R$^{1a}$ is phenyl, pyridine, naphthalene, piperidine, or pyrrolidine; each optionally substituted with halo, alkoxy, or alkyl.

In another aspect this invention provides a compound of formula VI wherein:

R$^1$ is OMe;

R$^b$ is OMe;

q is 2–3;

v is 2–3;

R is Ph optionally substituted with halo.

In another aspect this invention provides a compound of formula I where

R$^2$ is piperidine;

R is Ph, 4-Cl—Ph;

R$^{1a}$ is phenyl;

v is 2;

q is 3.

In another aspect this invention provides a compound of formula I which is (6,7-dimethoxy-3-styryl-quinoxalin-2-yl)-[3-(1-phenethyl-piperidin-4-yl)-propyl]-amine.

In another aspect this invention provides a compound of formula I which is selected from the group consisting of 2-(4-chloro-phenoxymethyl)-8-methoxy-3-(3-piperidin-4-yl-propyl)-3H-quinazolin-4-one hydrochloride; 3-(3-[1,4'] bipiperidinyl-1'-yl-propyl)-2-(4-chloro-phenoxymethyl)-8-methoxy-3H-quinazolin-4-one dihydrochloride; 8-methoxy-2-(5-methyl-[1,3,4]thiadiazol-2-ylsulfanylmethyl)-3-(3-piperidin-4-yl-propyl)-3H-quinazolin-4-one hydrochloride; 2-[2-(4-chloro-phenyl)-vinyl]-8-hydroxy-3-[3-(1-phenethyl-piperidin-4-yl)-propyl]3H-quinazolin-4-one; 2-[2-(4-chloro-phenyl)-vinyl]-3-[3-(1-phenethyl-piperidin-4-yl)-propyl]-8-(3-piperidin-1-yl-propxy)-3H-quinazolin-4-one; and (6,7-dimethoxy-3-styryl-quinoxalin-2-yl)-(3-piperidin-4-yl-propyl)-amine hydrocloride.

In another aspect this invention provides a compound of formula II wherein:

R$^1$ is H, Me, (CH$_2$)$_3$piperidine;

R$^b$ is H, OMe, Cl, F;

R' is CH$_2$OR;

R is phenyl optionally substituted with Cl, F, OMe;

R" is (CH$_3$)$_3$R$^2$;

R$^2$ is piperidine, or pyrrolidine each optionally substituted with (CH2)$_v$R1a v is 2–4; and R$^{1a}$ is phenyl, pyridyl, piperidine, or pyrrolidine; wherein the phenyl and pyridyl may be optionally substituted with Cl, or halo.

In another aspect this invention provides a compound of formula II which is 2-(4-chloro-phenoxymethyl)-8-methoxy-3-{3-[1-(3-piperidin-1-yl-propyl)-piperidin-4-yl]-propyl}-2,3-dihydro-1H-quinazolin-4-one.

In another aspect this invention provides a compound of formula III wherein:

R$^1$ is OMe or O(CH$_2$)$_3$piperidine;

R$^b$ is H, Cl or F;

R' is CH=CHR or CH$_2$OR;

R is Ph optionally substituted with Cl, F or OMe;

R" is (CH$_2$)$_3$R$^2$;

R$^2$ is piperidine or pyrrolidine optionally substituted with (CH$_2$)$_v$R1a v is 2–4; and R$^{1a}$ is phenyl, pyridyl, piperidine or pyrrolidine; wherein the phenyl and pyridyl are optionally substituted with Cl or halo.

In another aspect this invention provides the compound of formula III which is 3-(4-chloro-phenoxymethyl)-5-methoxy-2-{3-[1-(3-piperidin-1-yl-propyl)-piperidin-4-yl]-propyl}-2H-benzo[e][1,2,4]thiadiazine 1,1-dioxide.

In another aspect this invention provides a compound of formula IV wherein:

$R^1$ is Me or H;

$R^b$ isMe or H;

R' is CH=CHR or $CH_2OR$;

R is Ph optionally substituted with Cl, F or OMe;

R" is $(CH_2)_3R^2$;

$R^2$ is piperidine or pyrrolidine each optionally substituted with $(CH_2)_v R1a$;

v is 2–4;

$R^{1a}$ is phenyl, pyridyl, piperidine or pyrrolidine; wherein the phenyl or pyridyl are optionally substituted with Cl, or halo.

In another aspect this invention provides a compound of formula IV which is 6-(4-chloro-phenoxymethyl)-1,3-dimethyl-5-{3-[1-(3-piperidin-1-yl-propyl)-piperidin-4-yl]-propyl}-1,5-dihydro-pyrazolo[3,4-d]pyrimidin-4-one.

In another aspect this invention provides a compound of formula V wherein:

$R^1$ is OMe or $O(CH_2)_3$piperidine;

$R^b$ is H;

R' is CH=CHR or $CH_2OR$;

R is Ph optionally substituted with Cl, F or OMe;

R" is $(CH_2)_3R^2$;

$R^2$ is piperidine or pyrrolidine each optionally substituted with $(CH_2)_v R1a$;

v is 2–4; and $R^{1a}$ is phenyl, pyridyl, piperidine or pyrrolidine; wherein the phenyl or pyridyl is optionally substituted with Cl, or halo.

In another aspect this invention provides the compound of formula V which is [2-(4-chloro-phenoxymethyl)-8-methoxy-quinazolin-4-yl]-{3-[1-(3-piperidin-1-yl-propyl)-piperidin-4-yl]-propyl}-amine.

In another aspect this invention provides a pharmaceutical formulation, comprising, as an active ingredient, a compound of formulae I–VI in combination with one or more pharmaceutically acceptable carriers, diluents, or excipients, therefor.

In another aspect this invention provides a method of treating a condition associated with an excess of neuropeptide Y, which comprises administering to a mammal in need thereof an effective amount of a compound of formulae I–VI.

This invention also provides a pharmaceutical formulation, comprising, as an active ingredient, a compound selected from formula I to VI in combination with one or more pharmaceutically acceptable carriers, diluents, or excipients, therefor.

This invention further provides a compound selected from formula I to VI for use in treating a condition associated with an excess of neuropeptide Y, or a related peptide.

This invention also provides a method of treating a condition associated with an excess of neuropeptide Y, which comprises administering to a mammal in need thereof an effective amount of a compound selected from formula I to VI.

This invention provides the use of a compound selected from formula I to VI for the manufacture of a medicament for the treatment of a condition associated with an excess of neuropeptide Y.

Ths invention provides a pharmaceutical formulation adapted for the treatment of a condition associated with an excess of neuropeptide Y, comprising of a compound selected from formula I to VI.

In another aspect this invention provides a method of inhibiting or alleviating a pathological condition or physiological disorder in a mammalian subject characterized by or associated with an excess of neuropeptide Y which comprises administering to said subject an effective amount of a compound of formulae I to VI.

The compounds of formulae I to VI are basic in nature and are capable of forming a wide variety of salts with various inorganic and organic acids. The acids that may be used to prepare pharmaceutically acceptable acid addition salts of those compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, fumarate, gluconate, glucaronate, saccharate, formate, benzoate, glutamate, methanesulfonate, ethanesulfonate, benzenesulfonate, and p-toluenesulfonate.

Compounds that interact with NPY receptors and inhibit the activity of neuropeptide Y at those receptors are useful in treating numerous disorders associated with neuropeptide Y. This invention therefore provides a method of using compounds of Formula I which selectively bind to neuropeptide Y receptors and are useful in treating feeding disorders such as obesity and bulimia as well as disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemmorrhage, depression, anxiety, schizophrenia, and dementia;

conditions related to pain or nociception;

diseases related to abnormal gastrointestinal motility and secretion, such as different forms of ileus, urinary incontinence, and Crohn's disease;

abnormal drink and food intake disorders, such as anorexia and metabolic disorders; diseases related to sexual dysfunction and reproductive disorders; conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

DETAILED DESCRIPTION OF THE INVENTION

The preparation of compounds of Formulae I–VI of the present invention may be carried out in sequential or convergent synthetic routes. Syntheses describing the preparation of the compounds of the invention are shown in the following Schemes. The skills required for carrying out the reaction and purification of the resulting products are known to those in the art. Purification procedures include silica gel chromatography, distillation, filtration, etc.

In the scientific literature, derivatives of quinazolinones are already known to possess different biological activities such as calcium uptake inhibiting activity (U.S. Pat. No. 5,556,860), anti-hypertensive activity (U.S. Pat. No. 5,405,849), antianginal activity (U.S. Pat. No. 5,482,941), thymidylate synthase inhibiting activity (U.S. Pat. No. 5,561,133) and anti-mitotic activity (J. Med. Chem. 1990, 33(6),1721–8). Quinazoline analogs are known in the literature to exhibit biological activities such as bactericidal, tuberculostatic, and/or virucidal activities (Khim.-Farm. Zh. (1975), 9(11), 12–18; Khim.-Farm. Zh. (1982), 16(2), 183–8). Quinazolines have also been shown to be useful for treating bone deficit disorders (WO 9817267). Derivatives of quinoxalines exhibit anti-inflammatory activity (Ger. Offen., DE 2357186) and glucagon receptor antagonist activity (Collins, J. L. et al., Bioorg. Med. Chem. Lett., 1992, 2 (9), 915–918). 4H-1,2,4-Benzothiadiazine 1,1-dioxide analogs have been shown to have anti-bacterial and anti-hypertensive activities (JP 60025984; J Med. Chem. 1972, 15(4), 394–400) and anti-mitotic activity (J Med. Chem. 1990, 33(6),1721–8).

The compounds of Formula I can be prepared by processes known in the literature. See The Chemistry of Heterocyclic Compounds (A. Weissberger, et. Al, eds, 1979). Many of the synthetic methods are also documented in A. R. Katrizky, Handbook of Heterocyclic Chemistry, Pergamon Press, 1985, New York, N.Y. and may be used to synthesize a variety of heterocylic compounds of the present invention.

Scheme 1a

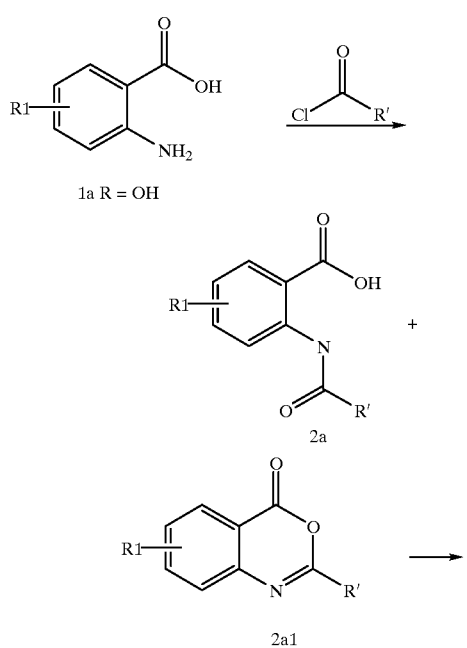

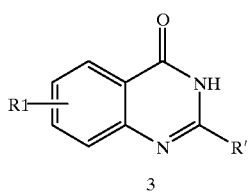

3

Scheme 1b

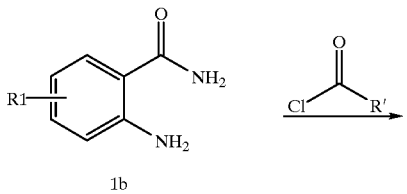

1b

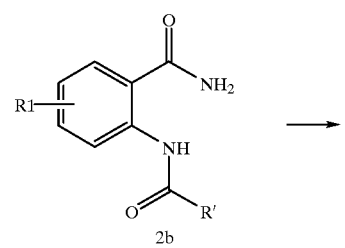

2b

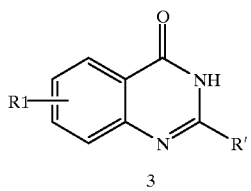

3

Quinazolinones of formula 3 may be synthesized as described in Schemes 1a-b. Coupling of the anthranilic acid 1a with an acid chloride in the presence of an activating agent such a 4-dimethylaminopyridine in a polar solvent such as pyridine provides a mixture of the intermediate 2a and the benzoxazin-4-one 2a1. Treatment of this mixture in refluxing formamide gives the quinazolinone 3. The anthranilic amides 1b (R=NH$_2$) can be converted into the quinazolinone compounds of formula 3 by first treating with an acyl chloride (R'COCl) and an activating agent such as DMAP in a polar solvent such as pyridine or in a chlorinated solvent such as methylene chloride at temperatures between 0° C. and 23° C. Dehydration of 2b using a base such as sodium ethoxide in a suitable solvent such as ethanol provides the desired analogs (see Lee et al., J. Med. Chem., 1995, 38, 3547–3557). It is generally preferred that during the dehydration step the solvent be heated, preferably to the boiling point.

Those compounds of formula 3 wherein R1 is not hydrogen can be prepared from commercially available anthranilic acids or by methods taught in the literature.

Scheme 2

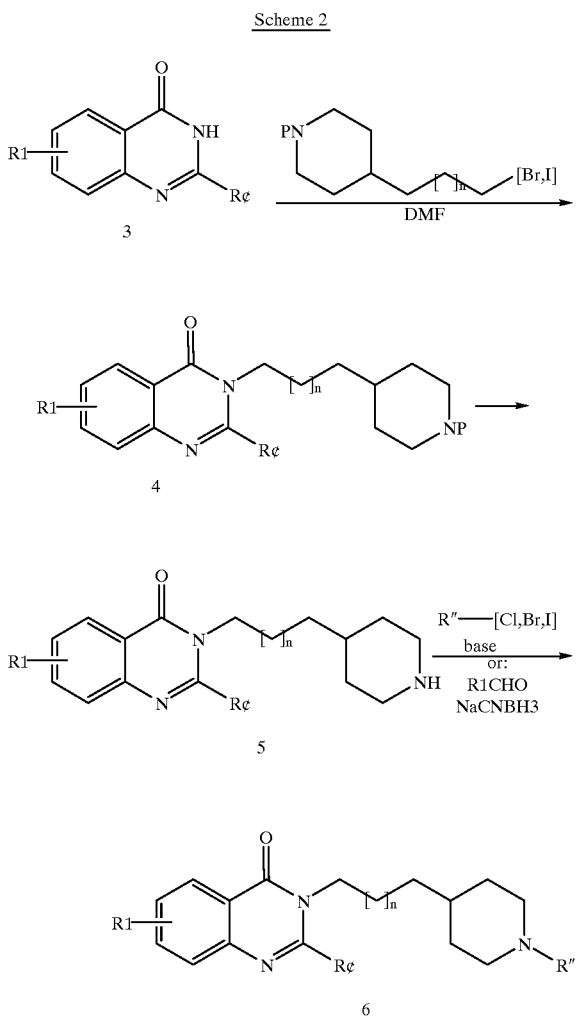

The N-alkylation of quinazolinones of structure 3 may be carried out as described in Scheme 2. Compound 3 is first deprotonated with a suitable base such as sodium hydride in a polar aprotic solvent such as DMF or THF, then treated with an alkyl halide to give a mixture of N- and O-alkylated products. The desired product can be separated using methods known in the art such as $SiO_2$-gel chromatography. Further elaboration of intermediates such as 5 can be carried out using a second alkylating agent in the presence of a base such as potassium carbonate in a polar aprotic solvent. Alternatively, compounds of formula 5 can be condensed with aldehydes in a suitable protic solvent such as methanol, then treated with a suitable chemical reducing agent such as sodium borohydride or sodium cyanoborohydride in the presence of a catalytic amount of acid.

Compounds of formula 6 wherein R1 is a methoxy group can be further elaborated by treatment with concentrated HBr in refluxing acetic acid to give 6, R=OH, which can then be treated with an alkylating agent in the presence of a base such as potassium carbonate in a solvent such as DMF. Alternatively, compound 6, R=OH can be treated with triflic anhydride in the presence of a base in a suitable solvent such as methylene chloride to give 6, R=OTf. This intermediate can then undergo Suzuki-coupling reactions with aryl boronic acids using a suitable catalysts such as $PdCl_2$ or Heck reactions with vinyl or acetylenic compounds in the presence of a suitable palladium catalyst in a suitable solvent such as diethylamine. Compounds of formula 6 wherein R=halide can be furthered elaborated using a palladium-catalyzed amination reaction (see Wolfe, J. P.; Buchwald, S. L. *Tetrahedron Letters*, 1997, 38, 6359–6362; Wagaw, S.; Rennels, R. A.; Buchwald, S. L. *JACS*, 1997, 119, 8451–8458). Compounds of formula 6, R=$CO_2$Et can be further elaborated by a number of methods known in the art. For example, when R=$CO_2$Et, the ester (provided it is the only ester in the molecule) can be saponified into the carboxylic acid which can be further derivatized to amides or other esters. The carboxylic acid 6 can be converted into its next higher homolog or to a derivative of the homologous acid such as amide or ester by an Arndt-Eistert reaction. The carboxylic acid can also be converted to an amino group via a Curtius Rearrangement using diphenylphosphoryl azide. Treatment of compounds of formula 6 (R=$NH_2$) with aldehydes in a suitable solvent such as HOAc or MeOH, followed by treatment with a reducing agent such as $NaBH_4$ will give amines.

Scheme 3

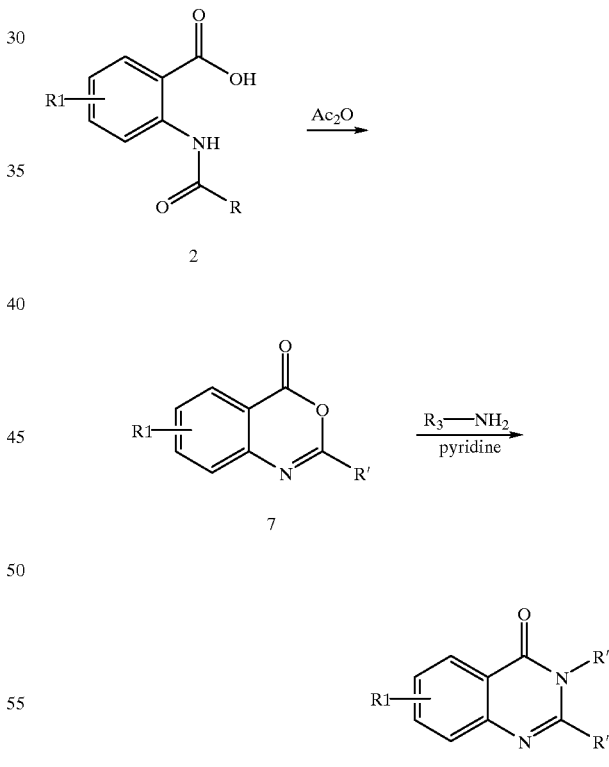

An alternative synthesis of quinazolinones is illustrated in Scheme 3. Compound 2 is first dehydrated using refluxing acetic anhydride to give the benzoxazin-4-one 7. Treatment of 7 with an amine such as $R_3$—$NH_2$ in a suitable solvent such as pyridine at elevated temperatures (preferentially 115° C.) provides N-substituted quinazolinones such as 8.

Scheme 4

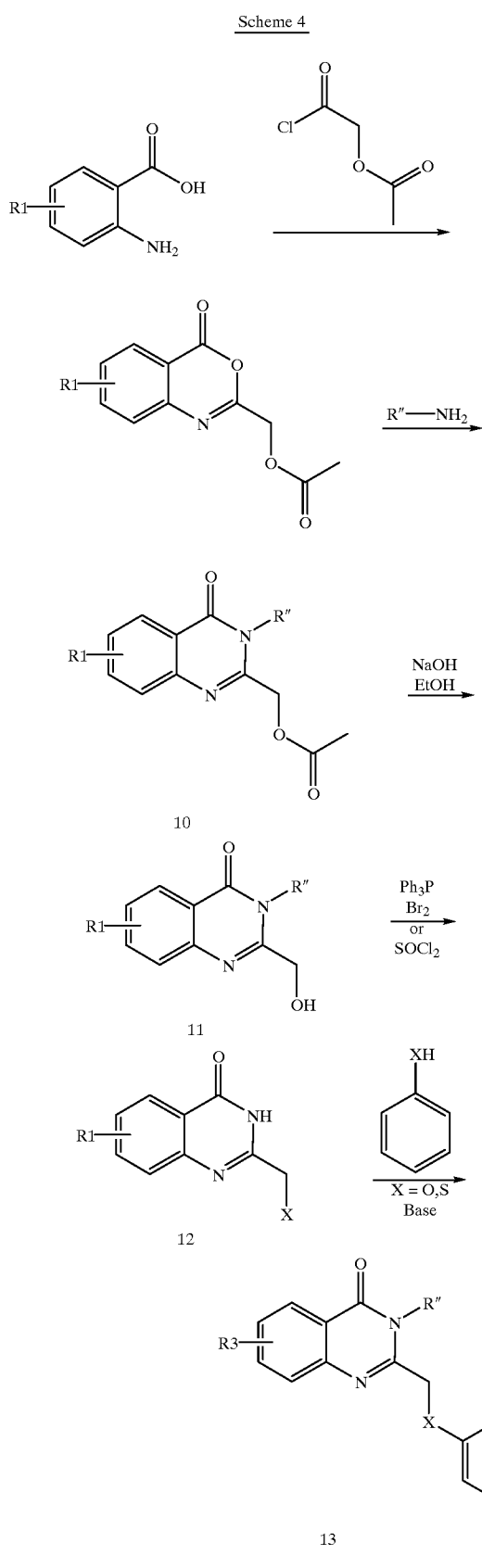

The preparation of quinazolinones substituted at C-2 with aryloxy or arylthio substituents can be prepared as shown in Scheme 1 using aryloxyacetyl chloride. An alternative synthesis of such compounds is illustrated in Scheme 4. The benzoxazin-4-one (prepared as shown in Scheme 3 from the appropriately substituted anthranilic acid and acyl chloride) is first treated with an amine in suitable solvent such as ethanol, pyridine or acetic acid to give 10. The removal of the acetate group can be achieved using base (preferably aqueous sodium hydroxide) in an alcoholic solvent such as methanol. Treatment of 11 with a chlorinating agent such as thionyl chloride or oxalyl chloride or with an brominating agent such as triphenylphosphine and bromine provides 12. This compound can be treated with phenols, thiophenols, etc in the presence of bases such as potassium bicarbonate to give derivatives of formula 13.

Scheme 5

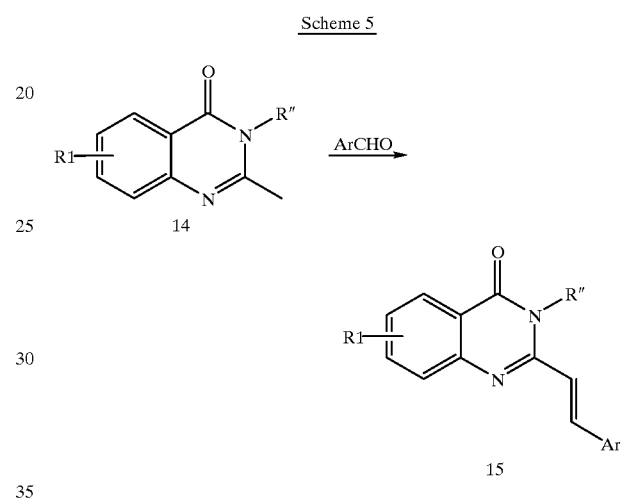

The preparation of C-2 styrenyl quinazolinones is illustrated in Scheme 5. Condensation of 14 with an aryl aldehyde in a solvent such as acetic acid provides 15 (see Jiang et al, *J. Med. Chem.*, 1990, 33,1721–1728). It is generally preferred that the solvent be heated, preferably to its boiling point.

Scheme 6

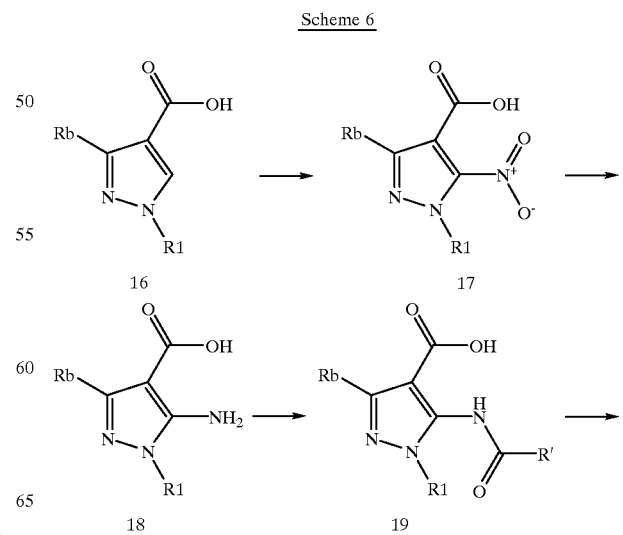

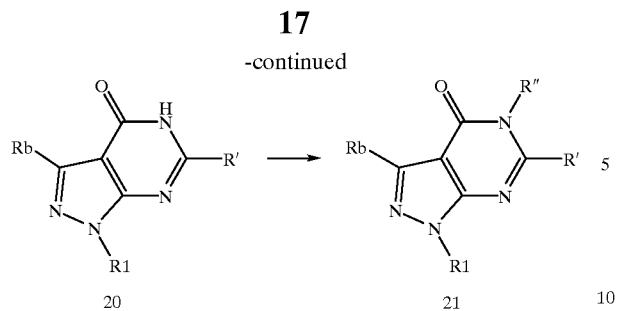

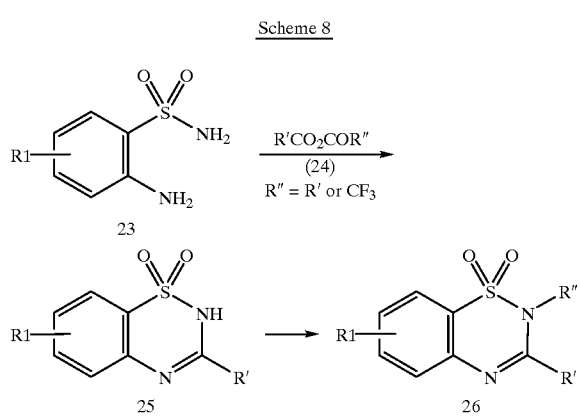

The preparation of pyrazopyrimidones is shown in Scheme 6. Nitration of the pyrazolecarboxylic acid 16 provides 17 which can be reduced either by catalytic hydrogenation with hydrogen in the presence of palladium catalysts in an alcoholic solvent or by a reducing agent such as $SnCl_2 \cdot xH_2O$ in a suitable solvent such as methanol or ethanol. The 2-aminopyrazalone-1-carboxylic acid can be then converted into the desired substituted pyrimidones by synthetic routes described earlier. The methods described in Scheme 6 can be used to convert a number of commercially available five- and six-membered heterocyclic carboxylic acids into the corresponding heterocylic pyrimidones.

Scheme 7

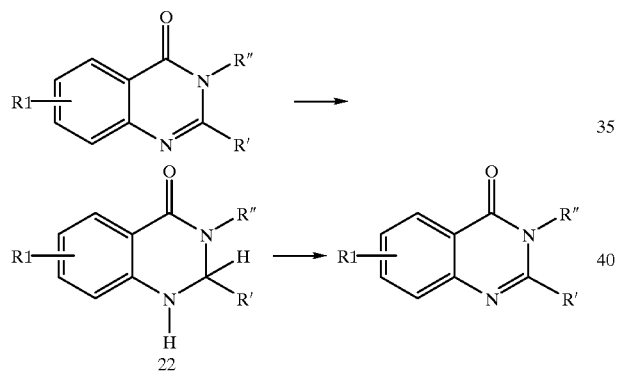

The preparation of 2,3-dihydroquinazolinone is illustrated in Scheme 7. Reduction of the quinazolinone with $H_2$ gas using a suitable catalyst such as Pd/C in the presence of an acid such as concentrated HCl in an alcoholic solvent such as ethanol or methanol provides the desired 2,3-dihydroquinazolinone 22. Alternatively, the quinazolinone may be reduced with a hydride reducing agent such as LAH in a polar aprotic solvent such as THF. It is generally preferred that the solvent be heated, preferably to the boiling point of the solvent.

Elaboration of quinazolinone derivatives may result in the formation of the undesired 2,3-dihydroquinazolinone analog. This dihydro compound may be oxidized back to the desired quinazolinone derivative by treatment with an oxidizing agent such as $MnO_2$ in a suitable solvent such as methylene chloride.

2H-Benzo[e][1,2,4]thia-diazine 1,1-dioxides of formula 26 can be synthesized by the method described in Scheme 8. Treatment of a 2-amino-arylsulfonamide 23 with a mixed or symmetrical anhydride of formula 24 in a suitable solvent such as methylene chloride or pyridine, followed by cyclo-condensation in a solvent such as aqueous ammonium hydroxide provides compounds of formula 25 (see Bierbaum, B. A. et al.; *J. Med.Chem.*, 1963, 6, 272–275 or Whitehead, C. W., *J. Org. Chem.*, 1961, 26, 2809–2813). A symmetrical anhydride can be prepared from the corresponding acid by treatment with a dehydrating agent such as $P_2O_5$. The mixed anhydride 24 wherein $R''=CF_3$ can be prepared by first treating the corresponding acid with trifluoroacetic acetic acid anhydride in a suitable solvent such as methylene chloride. Compounds of formula 26 can be synthesized from 25 by treatment with a suitable base such as sodium hydride and an alkylating agent in a polar, aprotic solvent such as DMF.

Scheme 9

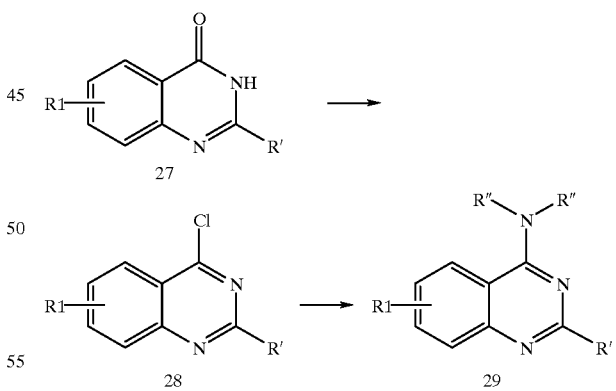

The synthesis of 2-aminoquinazolines is shown is Scheme 9. Chlorination of quinazolinones 27 with $POCl_3$ or $SOCl_2$ in a suitable solvent such as methylene chloride or dichloroethane provides the 4-chloro-quinazoline 28. Treatment of 28 with an amine in a suitable solvent such as ethanol or IPA provides the desired compounds. It is generally preferred that the solvent be heated, preferably to the boiling point of the solvent.

Scheme 10

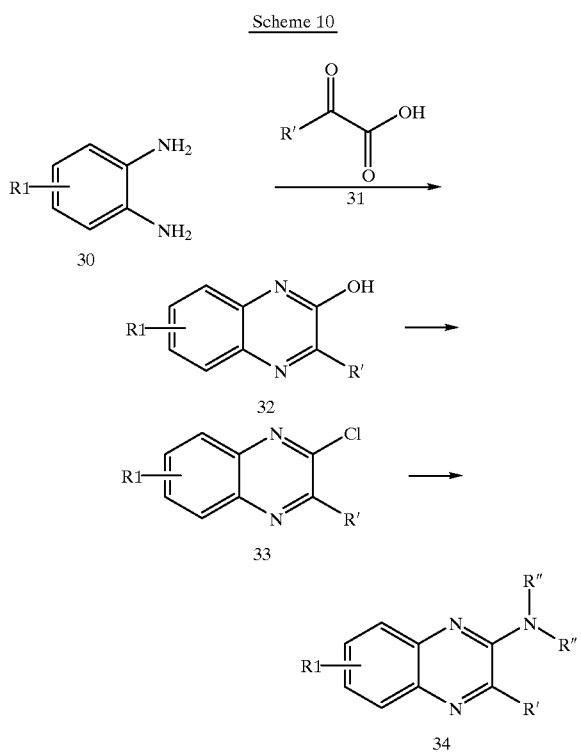

Quinoxalines of formula 34 can prepared as shown in Scheme 10. Condensation of 1,2-phenylenediamines of structure 30 with a keto-acid (31) in a solvent such as acetic acid/water provides the 2-hydroxy-quinoxaline 32 (see Collins, J. L. et al., Bioorg. Med. Chem. Lett., 1992, 2 (9), 915–918). Chlorination of 32 with neat POCl₃, followed by treatment with an amine in a suitable polar solvent such as refluxing ethanol provides the desired compounds.

a suitable catalyst such as Pd on carbon in a solvent such as ethanol or methanol provides the phenylethyl analog 37. Alternatively, the quinoxaline 38 with a suitable protecting group for the 2-hydroxy moiety can be brominated with NBS and a free radical initiator such as AIBN or benzoyl peroxide in a chlorinated solvent such as carbon tetrachloride under reflux temperatures to yield 39. This compound can be treated with a phenol in the presence of a base such as potassium carbonate in a polar, aprotic solvent such as DMF to give 40. Removal of P (protecting group) in 40 by known methods provides 2-hydroxyquinaxoline 32 which can be converted into various analogs by standard methods as described above.

The pharmaceutical utility of compounds of this invention is indicated by the following assay for human NPY1 receptor activity.

Assay for-Human NPY1 Receptor Binding Activity

The procedure used is similar to that described by Gordon et al. (J. Neurochem. 55:506–513,1990). SK-N-MC cells were purchased from ATCC (Rockville, Md.). Cells were maintained at 37° C. and 5% $CO_2$ in Dulbecco's modified essential media (DMEM) with L-glutamine and 110 mg/L sodium pyruvate, which was supplemented with 10% fetal bovine serum and 25 mM HEPES (pH 7.3). The binding assay was performed in 24-well plates (Falcon) when the cells were confluent. Taking care not to disturb the cells on the bottom of the wells, the media was aspirated, and 0.5 ml of Dulbecco's phosphate buffered saline (DPBS) with calcium and magnesium were added to each well. The DPBS was aspirated and an additional aliquot of DPBS was added and aspirated. To begin the assay, binding buffer consisting of serum-free DMEM containing 0.5% bovine serum albumin, 0.1% bacitracin and 0.1 mM phenylmethylsulfonylfluoride was added to each well. The cells and the binding buffer were preincubated for 30 minutes at room temperature, at which point the drug dilution and [$^{125}$I]PYY (NEN-DuPont: 50000–75000 cpm ~50 pM) were added to yield a final volume of 250 ul. Nonspecific binding was defined with 1 mM NPY (porcine or human, Bachem Calif.).

Scheme 11

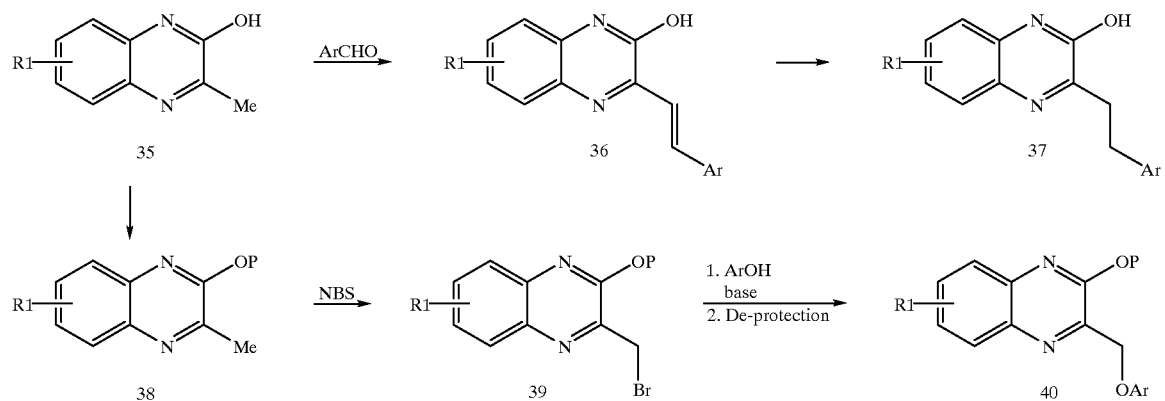

Quinoxalines of formula 32 where R'=Me can be further elaborated by known methods. For example, the quinoxaline 35 can be condensed with an aromatic aldehyde in a suitable solvent such as acetic acid and sulfuric acid under reflux conditions to give the styrenyl analog 36 (see Kadin, S. B., Ger Offen., DE 2357186). Reduction of 36 with $H_2$ gas and After a 3 hour incubation at room temperature, the plates were then put on ice and the wells were aspirated. The cells were washed 4–6 times with 0.5 ml of ice-cold DPBS. A dilute solution of Triton X-100 (1%) was then added to each well. After approximately 1 hour at room temperature, an aliquot from each well was transferred to a 12×75 mm test tube, and the amount of [$^{125}$I] was quantitated on a gamma counter with an efficiency of 80–85% (Genesys 5000, Laboratory Technologies). IC$_{50}$ values were calculated with the non-linear curve fitting program RS/1 (BBN Software Products Corp., Cambridge, Mass.).

[$^{125}$I]]PYY Binding at Human NPY Receptors Expressed in Sf9 Cells

Baculovirus-infected Sf9 cells expressing recombinant human H17 subtype of NPY receptors are harvested at 48 hours. At the time of harvest, cell pellets are resuspended in lysis buffer (20 mM Tris-HCl, pH 7.4, 5mM EDTA, 0.5 ug/ml leupeptin, 2 ug/ml Aprotonin and 200 uM PMSF) and homogenized using a Polytron (setting 3, 25–30 seconds). Homogenates are centrifuged at 4° C. for 5 minutes at 200 ×g (1500 rpm) to pellet the nuclei. The supernatant is collected into a fresh tube and centrifuged at 48,000×g for 10 minutes. Pellets are washed once in lysis buffer and centrifuged. The final pellet is resuspended in PBS and stored in aliquots at −80° C. Purified membranes are washed using PBS and resuspended in binding buffer (50 mM Tris-HCl, pH 7.4, 5 mM Kcl, 120 NM NaCl, 2mM CaCl$_2$, 1 mM MgCl$_2$, 0.1% bovine serum albumin (BSA)). Membranes (20 ug/reaction tube) are added to polypropylene tubes containing 0.030 nM [$^{125}$I]PYY(porcine), displacers ranging from 10$^{-12}$ M to 1-$^{-5}$ M, and buffer to yield a final volume of 0.250 mL. Nonspecific binding is determined in the presence of 1 uM NPY(human) and accounts for 10% of total binding. Following a 2 hour incubation at room temperature, the reaction is terminated by rapid vacuum filtration. Samples are filtered over presoaked GF/C Whatman filters (1.0% polyethylenemine) and rinsed 2 times with 5 mLs cold binding buffer without BSA. A gamma counter is used to count filters with an efficiency of 85%. IC$_{50}$ values were calculated with the non-linear curve fitting program RS/1 (BBN Software Products Corp., Cambridge, Mass.).

Functional Assay for NPY Receptors Expressed in Oocytes

Experiments were performed in Xenopus oocytes. Oocytes were prepared and maintained using standard protocols (Dascal and Lotan, in *Methods in Molecular Biology; Protocols in Molecular Neurobiology*, eds. Longstaff & Revest, Humana, Clifton, N.J., 13: 1992). For the present experiments, oocytes were obtained from 6 frogs. Oocytes were recorded from 2–7 days following coinjection of GIRKI and he H17 NPY-1 or NPY-5 subtype mRNA (25 ng of each, 50 nL total volume).

Two electrode voltage clamp recordings were carried out using a Warner Instruments Oocyte clamp OC 725B. Data were collected on a Macintosh microcomputer and analyzed using Superscope software. Voltage and current electrodes were pulled from glass tubing (1.5 mM O.D.) on a Brown/Flaming micropipet puller (Sutter Instruments, model P-87). Electrodes contained 3M Kcl and had resistance of 0.5–2 Mohms. Oocytes were bathed in normal external solution containing; 90 mM NaCl, 1 mM Kcl, 1 mN MgCl$_2$, 1 mM CaCl$_2$, 5 mM HEPES, pH=7.4. Before NPY agonists or antagonists were introduced, a high K$^+$, solution containing; 1 mM NaCl, 90 mM Kcl, 1 mM MgCl$_2$, 1 mM CaCl$_2$, 5 mM HEPES was applied to permit recording of the inwardly rectifying K$^+$ current. Drugs were applied diluted in the high K$^+$ media.

100 $\mu$M stocks of NPY, PP or NPY peptide fragments or PYY peptide fragments were prepared in water and frozen until needed.

Oocytes were voltage-clamped at −80 mV with two electrodes. Oocytes were initially superfused with normal external medium (approximate flow rate 4 ml/min.). Before drugs were applied, cells were superfused with high K$^+$ solution to permit activation of the inwardly rectifying K$^+$ current. In oocytes coinjected with NPY receptor and GIRK1 mRNA, NPY agonists induced an additional inward current over the resisting K$^+$ current caused by high K$^+$ medium. Because responses desensitized at slow, but varying rates, cumulative dose applications were administered to generate concentration response curves. Two to four doses of agonists to each cell. Agonist dose responses in each cell were normalized against the response to a maximal concentration of human NPY. Dose response curves were fit with a logistic equation using Kaleidagraph software (Abelbeck software, Reading, Pa.).

The compounds of general formulae I–VI and pharmaceutically acceptable salts thereof (the active compounds) may be administered orally, topically, parenterally by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniquies. In addition, there is provided a pharmaceutical formulation comprising a compound of general formulae I–VI and a pharmaceutically acceptable carrier. One or more active compounds may be present in association with one or more non-toxic pharmaceutically acceptable carriers and/or diluents and/or adjuvants and if desired other active ingredients. The pharmaceutical compositions containing active compounds may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions of sweetening agents, flavoring agents, coloring agents and preserving agents in order to provide pharmaceutically elegant and palatable preparations. Tablets contain the active ingredient in admixture with non-toxic pharmaceutically acceptable excipients with are suitable for the manufacture of tablets. These excipients may be for example, inert diluents, such as calcium carbonate, sodium carbonate, lactose, calcium phosphate or sodium phosphate; granulating and disintegrating agents, for example, intert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with partial esters derived from fatty acids and a hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gum, for example gum acacia or gum tragacanth, naturally occurring phosphatides, for example soy bean, lecithin, and esters or partial esters derived from fatty acids and hexitol, anhydrides, for example sorbitan monoleate, and condensation products of the said partial esters with ethylene oxide, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The active compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Active compounds may be administered parenterally in a sterile medium. The drug, depending on the vehicle and concentration used can either be suspended or dissolved in the vehicle. Advantageously, adjuvants such as local anesthetics, preservatives and buffering agents can be dissolved in the vehicle.

Dosage levels of the order of from about 0.1 mg to about 15 mg of active compound per kilogram of body weight per day are useful in the treatment of the above-indicated conditions (about 0.5 mg to about 7 g per patient per day). The amount of active compound that may be combined with the carrier materials to produce a single dosage form will vary depending upon the host treated and the particular mode of administration. Dosage unit forms will generally contain between from about 1 mg to about 500 mg of an active compound.

It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

As a consequence of their action in treating pathological conditions the compounds of the present invention possess utility for treatment of ungulate animals such as swine, cattle, sheep, and goats. Active compounds of the invention can additionally be used for the treatment of household pets, for example companion animals such as dogs and cats. The administration of an active compound of formula I can be effected orally or parenterally. An amount of an active compound of formula I is administered such that an effective dose is received, generally a daily dose which, when administered orally to an animal is usually between 0.01 and 20 mg/kg of body weight, preferably between 0.05 and 10 mg/kg of body weight. Conveniently, the medication can be carried in drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active compound can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for treating domestic animals are generally prepared by mixing a compound of the invention with a sufficient amount of animal feed to provide from about $10^{-3}$ to 500 ppm of the compound in the feed of water.

In general, parenteral administration involves injection of a sufficient amount of the compounds of the present invention to provide the animal with 0.01 to 20 mg/kg/day of body weight of the active ingredient. The preferred dosage for poultry, swine, cattle, sheep, goats and domestic pets is in the range of from 0.05 to 10 mg/kg/day of body weight of active ingredient.

The term "treating" as used herein includes preventative (e.g., prophylactic), palliative and curative treatment.

By halo is meant chloro, bromo, iodo, or fluoro.

By alkyl is meant straight chain or branched saturated hydrocarbon.

Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched saturated alkyl bonded though an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The expression "pharmaceutically acceptable acid addition salts" is intended to include but is not limited to such salts as the hydrochloride, hydrobromide, hydroiodide, nitrate, hydrogen sulfate, dihydrogen phosphate, mesylate, maleate, and succinate. Such salts are conventionally prepared by reacting the free base form of the compound (I), (II) or (III) with an appropriate acid, usually one molar equivalent, and in a solvent. Those salts which do not precipitate directly are generally isolated by concentration of the solvent and/or addition of a non-solvent.

The expression "prodrug" refers to compounds that are drug precursors, which, following administration, release the drug in vivo via a chemical or physiological process (e.g., a prodrug on being brought to the physiological pH is converted to the desired drug form).

As used herein, the expressions "reaction-inert solvent" and "inert solvent" refers to a solvent or mixture of solvents which does not interact with starting materials, reagents, intermediates or products in a manner which adversely affects the yield of the desired product.

The chemist of ordinary skill will recognize that certain compounds of this invention will contain one or more atoms which may be in a particular sterochemical or geometric configuration, giving rise to stereoisomers and configurational isomers. All such isomers and mixtures thereof are included in this invention. Hydrates and solvates are also included.

Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

Compounds of this invention may be prepared with isotopic elements which may be radioactive. Such compounds, known as "labeled compounds" may be identified by conventional mass spectrometers or radiation detectors. These compounds are useful for determining the distribution of this compound in an animal body or to identify metabolities of the compound.

Other features and advantages will be apparent from the specification and claims which describe the invention.

EXAMPLES

The following Examples are provided to illustrate the invention. The Examples do not limit the invention which is defined by the claims.

Example 1

2-[2-(4-Chloro-phenoxy)-acetylamino]-3-methoxybenzoic acid (A) and 2-(4-chloro-phenoxymethyl)-8-methoxy-benzo[d][1,3]oxazin-4-one (B)

Mixture of

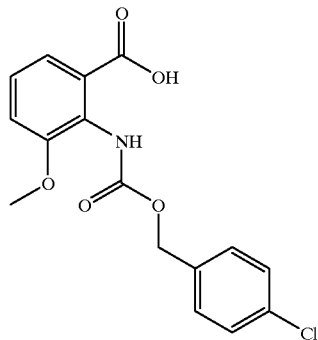

A and

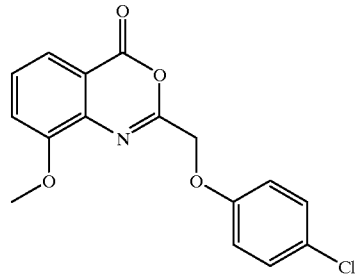

B

A solution of 4-chlorophenoxyacetyl chloride (6.1 g, 29.91 mmol) in toluene (40 mL) was added to a solution of 2-amino-3-methoxybenzoic acid (5 g, 29.91 mmol) and DMAP (367 mg, 3 mmol) in 100 mL pyridine at 5° C. The reaction mixture was stirred for 17 h and concentrated under vacuum. The residue was dissolved in EtOAc and washed with 10% aq HCl, dried over $Na_2SO_4$ and concentrated to give the product as a white solid. API-MS: 318, 336 (M+1). $^1$H NMR (300 MHz, d4-MeOH): d 7.5 (d, 1 H), 7.3 (m, 4 H), 7.05 (d, 1 H), 6.9 (d, 2 H), 4.68 (s), 4.65 (s), 3.85 (s, 3 H).

The following compounds in Table 1 were prepared by the method described in Example 1 using the appropriate acyl chloride (R'COCl):

TABLE 1

| Ex | R1 | R' | MS Method: M + 1 |
|---|---|---|---|
| 1a | C-8 Me | Me | API-MS: 176, 194 |
| 1b | C-8 OMe | Me | API-MS: 192, 210 |
| 1c | C-8 OMe | (4-chlorostyryl) | API-MS: 314, 332 |
| 1d | C-6 OMe | (4-chlorophenoxymethyl) | API-MS: 318 |
| 1e | C-7 OMe, C-8 OMe | (4-chlorophenoxymethyl) | API-MS: 348 |
| 1f | C-8 OMe | (phenoxymethyl) | API-MS: 284, 302 |
| 1g | C-8 OMe | (4-fluorophenoxymethyl) | API-MS: 302, 320 |

Example 2

2-(4-Chloro-phenoxymethyl)-8-methoxy-3H-quinazolin-4-one

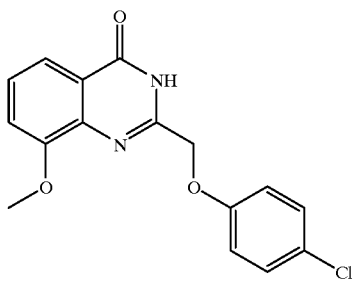

A solution of the product in Example 1 was heated in formamide ($^{125}$ mL) at 160° C. for 17 h. As the reaction mixture was cooled to room temperature, a solid precipitated out of solution. This solid was filtered and washed with formamide and isopropyl ether (300 mL) to yield the desired product as a colorless solid. API-MS: 317 (M+1). $^1$H NMR (300 MHz, $d_6$-DMSO): d 7.9 (d, 1 H), 7.63 (d, 1 H), 7.4 (3, 1 H), 7.3 (d, 2 H), 7.08 (d, 2 H), 5.0 (s, 2 H), 3.86 (3, 3 H).

The following compounds in Table 2 were prepared from the appropriately substituted benzoic acid/benzo[d][1,3] oxazin-4-one mixtures using the method described in Example 2.

TABLE 2

| Ex | R1 | R' | MS Method: M + 1 |
|---|---|---|---|
| 2a | C-8 Me | —Me | API-MS: 175 |
| 2b | C-8 OMe | —Me | API-MS: 191 |
| 2c | C-8 OMe | (4-chlorostyryl) | API-MS: 313 |
| 2d | C-6 OMe | (4-chlorophenoxymethyl) | API-MS: 317 |
| 2e | C-7 OMe, C-8 OMe | (4-chlorophenoxymethyl) | API-MS: 347 |
| 2f | C-8 OMe | (phenoxymethyl) | API-MS: 283 |
| 2g | C-8 OMe | (4-fluorophenoxymethyl) | API-MS: 301 |

Example 3

2-(4-Chloro-phenoxymethyl)-8-methoxy-3-(3-piperidin-4-yl-propyl)-3H-quinazolin-4-one hydrochloride Step A: Preparation of 4-{3-[2-(4-chloro-phenoxymethyl)-8-methoxy-4-oxo-4H-quinazolin-3-yl]-propyl}-piperidine-1-carboxylic acid tert-butyl ester

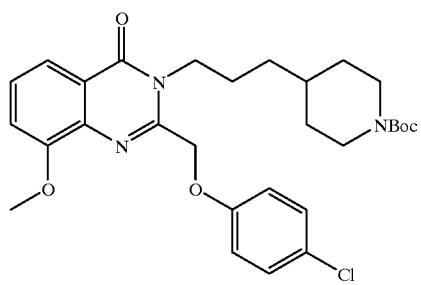

Sodium hydride (133 mg, 3.47 mmol) was added to a solution of 2-(4-chloro-phenoxymethyl)-8-methoxy-3H-quinazolin-1-one (1000 mg, 3.16 mmol) in DMF (30 mL). After 30 min, a solution of 4-(3-iodo-propyl)-piperidine-1-carboxylic acid tert-butyl ester (1226 mg, 3.47 mmol) in DMF (5 mL) was added. The reaction mixture was heated at 80° C. for 17 h, then was diluted with EtOAc, washed with sat'd aq NaCl, dried over $Na_2SO_4$ and concentrated. The crude residue was chromatographed on $SiO_2$-gel (30% EtOAc/hexanes) to give a mixture of the desired N-alkylated product (1030 mg) and the O-alkylated product (250 mg). API-MS: 542 (M+1). $^1$H NMR (300 MHz, CDCl3): d 7.85 (d, 2 H), 7.42 (3, 1 H), 7.2 (m, 3 H), 6.9 (d, 2 H), 5.17 (s, 2 H), 4.1 (t, 2 H), 3.97 (s, 3 H), 2.58 (t, 2 H), 1.8 (m), 1.6 (m), 1.4 (s, 9 H), 1.3 (m, 2 H), 1.0 (m, 2 H).

Step B: Preparation of 2-(4-chloro-phenoxymethyl)-8-methoxy-3-(3-piperidin-4-yl-propyl)-3H-quinazolin-4-one hydrochloride

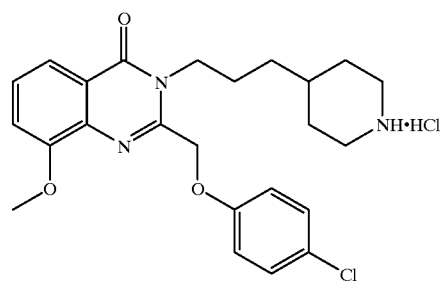

The product obtained in step A was dissolved in a solution of conc HCl/EtOH (1:3 mixture, 20 mL). The reaction mixture was stirred for 2 h, concentrated under vacuum and azeotroped with ethanol and heptane to give the desired product as a white solid. API-MS: 442 (M+1). $^1$H NMR (300 MHz, $d_4$-MeOH): d 7.81 (d, 1 H), 7.63 (t, 1 H), 7.55 (d, 1 H), 7.35 (d, 2 H), 7.1 (d, 2 H), 5.4 (s, 2 H), 4.15 (dd, 2 H), 4.05 (s, 3 H), 3.3 (m, 2 H), 2.9 (t, 2 H), 1.9 (m), 1.4 (m).

The following compounds in Table 3 were prepared by the methods described in Example 3 using the appropriately substituted quinazolinone derivative:

TABLE 3

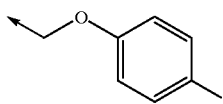

| Ex | R1 | R' | R" | MS Method: M + 1 |
|---|---|---|---|---|
| 3a | C-6 Cl | 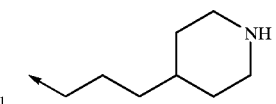 | 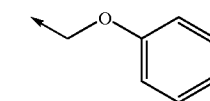 | PB-MS: 446 |
| 3b | C-6 OMe | 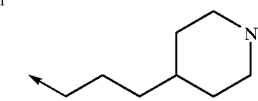 | 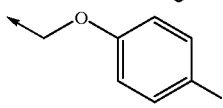 | PB-MS: 408 |
| 3c | C-6 OMe | 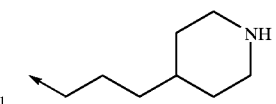 | 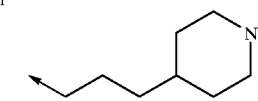 | PB-MS: 442 |
| 3d | C-7 OMe | " | 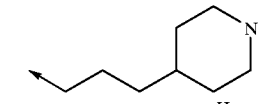 | API-MS: 442 |
| 3d | C-8 Me | " | 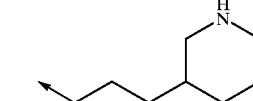 | API-MS: 427 |
| 3f | C-8 OMe | " | 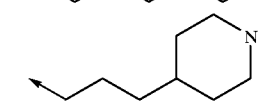 | API-MS: 442 |
| 3g | C-8 OMe | " | | API-MS: 442 |

TABLE 3-continued

| Ex | R1 | R' | R" | MS Method: M + 1 |
|---|---|---|---|---|
| 3h | C-8 OMe | 4-F-phenoxymethyl | 3-(piperidin-4-yl)propyl | API-MS: 424 |
| 3i | C-8 OMe | (E)-2-(4-chlorophenyl)ethenyl | 3-(piperidin-4-yl)propyl | API-MS: 439 |
| 3j | C-8 OMe | " | 3-(piperidin-3-yl)propyl | API-MS: 439 |

Example 4

2-(4-Chloro-phenoxymethyl)-8-methoxy-3-{3-[1-(3-piperidin-1-yl-propyl)-piperidin-4-yl]-propyl}-3H-quinazolin-4-one

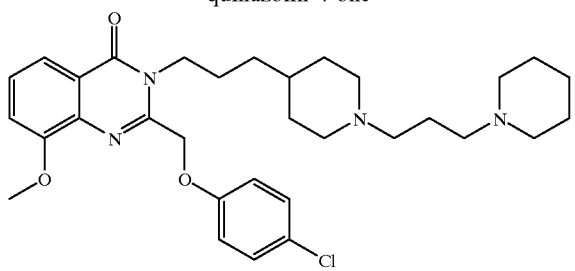

A solution of 2-(4-chloro-phenoxymethyl)-8-methoxy-3-(3-piperidin-4-yl-propyl)-3H-quinazolin-4-one (150 mg, 0.31 mmol), N-(3-chloropropyl)-piperidine hydrochloride (222 mg, 0.63 mmol), $K_2CO_3$ (87 mg, 0.63 mmol), KI (105 mg, 0.63 mmol) was heated at 80° C. in $THF/H_2O$ (3:1 mixture, 30 mL) for 17 h. After cooling to room temperature, the reaction mixture was diluted with EtOAc. The organic solution was separated and was washed with sat'd aq $NaHCO_3$, sat'd aq NaCl, dried and concentrated. The crude residue was chromatographed on $SiO_2$-gel using EtOAc/$NEt_3$ (10:1) to give the desired product as an oil. API-MS: 567.2 (M+1). $^1$H NMR (300 MHz, $d_4$-MeOH): d 7.75 (d, 1 H), 7.5 (t,1 H), 7.38 (d, 1 H), 7.3 (d, 2 H), 7.1 (d, 2 H), 5.25 (s, 2 H), 4.1 (m, 2 H), 4.0 (s, 3 H), 2.9 (m), 2.4–2.1 (m), 1.9–1.1 (m).

The following examples in Table 4 were prepared by the methods described in Example 4 using the appropriate alkylating agents:

TABLE 4

| Ex | Rb | R' | R1 | MS Method: M + 1 |
|---|---|---|---|---|
| 4a | C-8 Me | (4-chlorophenoxy)methyl | phenethyl | API-MS: 530 |
| 4b | C-8 OMe | phenoxymethyl | 3-(piperidin-1-yl)propyl | API-MS: 534 |

TABLE 4-continued
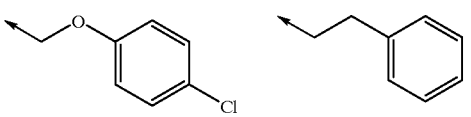
| Ex | Rb | R' | R1 | MS Method: M + 1 |
|---|---|---|---|---|
| 4c | C-8 OMe | 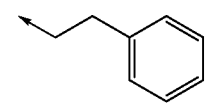 | 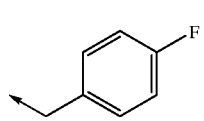 | API-MS: 547 |
| 4d | C-8 OMe | " | 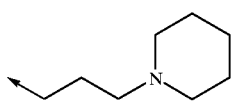 | API-MS: 551 |
| 4e | C-8 OMe | " | 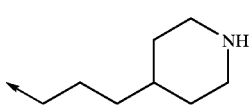 | API-MS: 568 |
| 4f | C-8 OMe | " | 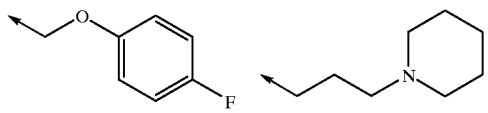 | API-MS: 568 |
| 4g | C-8 OMe | 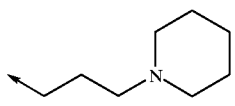 | 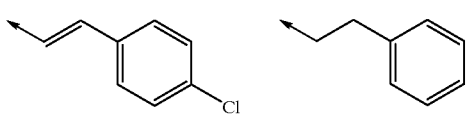 | API-MS: 551 |
| 4h | C-8 OMe | 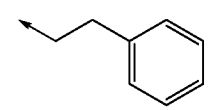 | 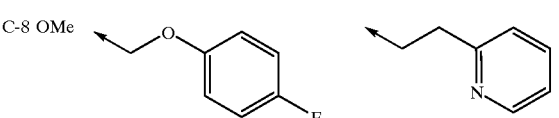 | API-MS: 543 |
| 4i | C-8 OMe | 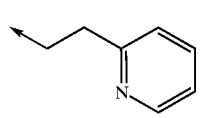 |  | API-MS: 531 |
| 4j | C-8 OMe | 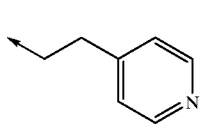 | 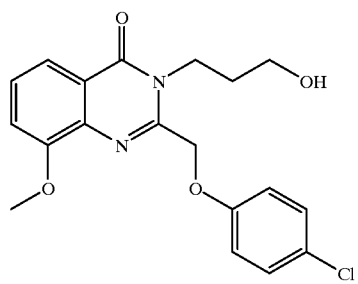 | API-MS: 531 |
Example 5
3-(3-[1,4']Bipiperidinyl-1'-yl-propyl)-2-(4-chloro-phenoxymethyl)-8-methoxy-3H-quinazolin-4-one dihydrochloride.
Step A: Preparation of 2-(4-chloro-phenoxymethyl)-3-(3-hydroxy-propyl)-8-methoxy-3H-quinazolin-4-one Sodium hydride (239 mg, 9.94 mmol) was added to a solution of 2-(4-chlorophenoxymethyl)-8-methoxy-3H-quinazolin-4-one (3000 mg, 9.47 mmol) in DMF (20 mL) at room temeprature. The reaction mixture was stirred for 30 min, then 3-bromopropanol (1448 mg, 0.94 mL, 10.42 mmol) was added. The reaction mixture was heated at 80° C. for 17 h, cooled to room temperature and diluted with EtOAc. The organic solution was washed with water, sat'd aq NaCl, dried and concentrated. The crude residue was purified using SiO$_2$-gel chromatography (50% EtOAc/hexanes) to give 1.1 g of the desired N-alkylated product. API-MS: 375 (M+1). $^1$H NMR (300 MHz, CDCl3): d 7.82 (d, 1 H), 7.4 (t, 1 H), 7.2 (m, 3 H), 7.9 (d, 2 H), 5.2 (s, 2 H), 4.36 (t, 2 H), 4.0 (s, 3 H), 3.58 (t, 2 H), 2.0 (t, 2 H).

Step B: Preparation of 2-($^4$-chloro-phenoxymethyl)-3-(3-iodo-propyl)-8-methoxy-3H-quinazolin-4-one

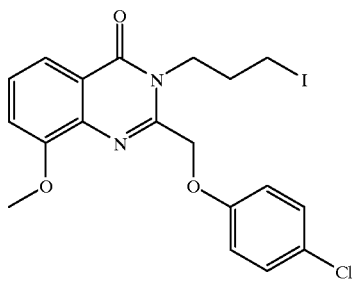

Iodine (1016 mg, 4 mmol) was added to a mixture of the product from Step A above, triphenylphosphine (1050 mg, 4 mmol) and imidazole (545 mg, 8 mmol) in toluene (20 mL) at 0° C. The reaction mixture was slowly allowed to warm to room temperature and was stirred for 17 h and diluted with CHCl$_3$. The organic solution was washed with sat'd aq NaHCO$_3$, sat'd aq NaCl, dried and concentrated. The crude residue was chromatographed on SiO$_2$-gel using 30% EtOAc/hexanes to yield the product as a yellow oil (450 mg, 35%). API-MS: 485 (M+1). $^1$H NMR (300 MHz, CDCl$_3$): d 7.8 (d, 1 H), 7.35 (t, 1 H), 7.2 (d, 2 H), 7.1 (d, 1 H), 6.9 (d, 2 H), 5.15 (s, 2 H), 4.1 (t, 2 H), 3.93 (s, 3 H), 3.9 (s, 3 H), 3.15 (t, 2 H), 2.23 (m, 2 H).

Step C: Preparation of 3-(3-[1,4']bipiperidinyl-1'-yl-propyl)-2-(4-chloro-phenoxymethyl)-8-methoxy-3H-quinazolin-4-one dihydrochloride

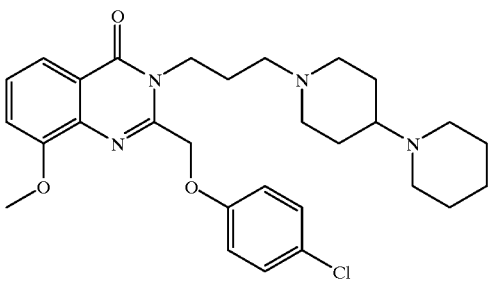

A mixture of the product from Step B (90 mg, 0.186 mmol), 4-piperidine-piperidine (125 mg, 0.743 mmol) and K$_2$CO$_3$ (102 mg, 0.743 mmol) in DMF (5 mL) was heated at 70° C. for 17 h. The reaction mixture was diluted with EtOAc and the organic solution was washed with H$_2$O, dried and concentrated. The crude residue was purified by SiO$_2$-gel chromatography (10% NEt$_3$/EtOAc). This product was dissolved in 4.0 M HCl in 1,4-dioxane (1 mL) and concentrated to give the desired compound (72 mg, 74%). API-MS: 526 (M+1). $^1$H NMR (300 MHz, d$_4$-MeOH): d 7.8 (d, 1 H), 7.5 (t, 1 H), 7.45 (d, 1 H), 7.3 (d, 2 H), 7.15 (d, 2 H), 5.35 (s, 2 H), 4.3 (t,2 H), 4.0 (s, 3 H), 3.8 (d, 1 H), 3.45 (d, 1 H), 3.1 (m, 2 H), 2.5–1.8 (m).

The following compounds were prepared by the methods described in Example 5:

TABLE 5

| Ex | R1 | R' | —R1a | MS Method: M + 1 |
|----|----|----|------|------------------|
| 5a | C-8 OMe | 4-chlorophenoxymethyl | piperidin-4-yl-pyrrolidine | API-MS: 511 |
| 5b | " | " | 4-phenylpiperazine | API-MS: 519 |
| 5c | " | " | 4-benzylpiperazine | API-MS: 533 |

TABLE 5-continued

[Structure: 3H-quinazolin-4-one core with N-propyl-R1a substituent, R' at C2, R1 at C8]

| Ex | R1 | R' | —R1a | MS Method: M + 1 |
|---|---|---|---|---|
| 5d | " | " | 4-hydroxy-4-phenylpiperidin-1-yl | API-MS: 534 |
| 5e | " | " | 4-[(4-fluorophenoxy)methyl]-...-piperazinyl with phenethyl | API-MS: 531 |
| 5f | " | " | 4-(3-phenylpropyl)piperazin-1-yl | API-MS: 545 |
| 5g | " | " | 4-(benzo[d][1,3]dioxol-5-ylmethyl)piperazin-1-yl | API-MS: 561 |

Example 6

2-[2-(4-Chloro-phenyl)-vinyl]-8-methoxy-3-{3-[1-(3-piperidin-1-yl-propyl)-piperidin-4-yl]-propyl}-3H-quinazolin-4-one Step A: Preparation of 4-[3-(8-methoxy-2-methyl-4-oxo-4H-quinazolin-3-yl)-propyl]-piperidine-1-carboxylic acid tert-butyl ester

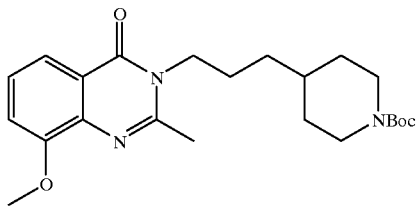

Sodium hydride (91 mg, 2.37 mmol) was added to a solution of 8-methoxy-2-methyl-3H-quinazolin-4-one (300 mg, 1.58 mmol) in DMF (30 mL). The reaction mixture was stirred at 80° C. for 0.75 h and cooled to room temperature, then a solution of 4-(3-iodo-propyl)-piperidine-1-carboxylic acid tert-butyl ester (837 mg, 2.37 mmol) in DMF (1 mL) was added. The reaction mixture was heated at 85° C. for 17 h and diluted with EtOAc. The organic solution was washed with water and sat'd aq NaCl, dried and concentrated. Purification on SiO$_2$-gel chromatography (50% EtOAc/hexanes) provided the desired product as a yellow oil. API-MS: 416 (M+1).

Step B: Preparation of 8-methoxy-2-methyl-3-(3-piperidin-4-yl-propyl)-3H-quinazolin-4-one

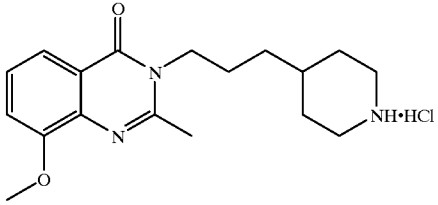

The product from Step A above was dissolved in conc HCl/EtOH (1:2 mixture, 18 mL) and was stirred for 1 h. The reaction mixture was concentrated under vacuum and azeotroped with EtOH (2×) to provide the desired product as a white solid. API-MS: 316 (M+1)

Step C: Preparation of 8-methoxy-2-methyl-3-{3-[1-(3-piperidin-1-yl-propyl)-piperidin-4-yl]-propyl}-3H-quinazolin-4-one

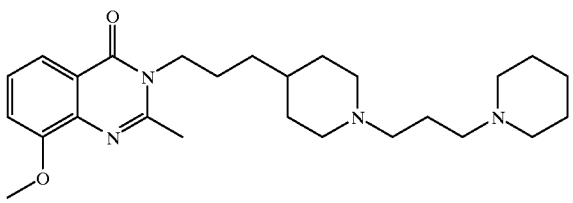

A mixture of the product from Step B (331 mg, 0.94 mmol), N-(3-chloropropyl)piperidine hydrochloride (666 mg, 1.88 mmol), potassium carbonate (260 mg, 1.88 mmol) and potassium iodide (312 mg, 1.88 mmol) in THF/H$_2$O (3:1 mixture, 40 mL) was heated under reflux for 17 h. The reaction mixture was cooled to room temperature and diluted with EtOAc. The organic solution was washed with sat'd aq NaHCO$_3$, sat'd aq brine, dried and concentrated. The crude residue was chromatographed on SiO$_2$-gel using a solvent gradient of 100% EtOAc to EtOAc/NEt$_3$ (10:1) to give the product as a yellow oil. API-MS: 441 (M+1). $^1$H NMR (300 MHz, CDCl$_3$): d 7.8 (d, 1 H), 7.3 (t, 1 H), 7.1 (d, 1 H), 4.03 (t, 2 H), 4.9 (s, 3 H), 3.9 (m), 2.7 (s, 3 H), 2.3 (m), 1.8–1.2 (m).

Step D: Preparation of 2-[2-(4-chloro-phenyl)-vinyl]-8-methoxy-3-{3-[1-(3-piperidin-1-yl-propyl)-piperidin-4-yl]-propyl}-3H-quinazolin-4-one

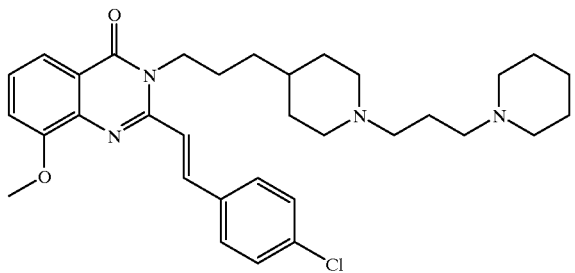

A solution of the product from Step C (144 mg, 0.33 mmol) and 4-chlorobenzaldehyde (46 mg, 0.33 mmol) in acetic acid (15 mL) was heated at 120° C. for 17 h. The reaction mixture was concentrated under vacuum and the residue was diluted with CHCl$_3$. The organic solution was washed with sat'd aq NaHCO$_3$, sat'd aq NaCl, dried and concentrated. Purification via SiO$_2$-gel chromatography using EtOAc/NEt$_3$ (10:1) yielded the desired product. API-MS: 563 (M+1). $^1$H NMR (300 MHz, CDCl$_3$): d 8.0 (d, 2 H), 7.8 (d, 1 H), 7.5 (d, 2 H), 7.38 (m, 3 H), 7.15 (d, 1 H), 7.0 (d, 2 H), 4.1 (t, 2 H), 4.0 (s, 3 H), 2.85 (m), 2.3 (m), 1.9–1.2 (m).

Example 7

8-Methoxy-2-(5-methyl-[1,3,4]thiadiazol-2-ylsulfanylmethyl)-3-(3-piperidin-4-yl-propyl)-3H-quinazolin-4-one Step A: Preparation of 4-[3-(2-bromomethyl-8-methoxy-4-oxo-4H-quinazolin-3-yl)-propyl]-piperidine-1-carboxylic acid tert-butyl ester

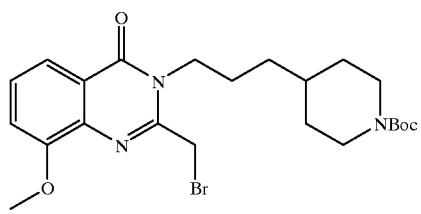

A mixture of the product from Example 6, Step A (2380 mg, 5.73 mmol), NBS (1530 mg, 8.6 mmol), AIBN (94 mg, 0.57 mmol) in CCl$_4$ (50 mL) was heated under reflux for 17 h. The reaction mixture was cooled to room temperature and filtered. The filtrate was concentrated under vacuum and the residue was purified by SiO$_2$-gel chromatography using 30% EtOAc/hexanes to give the desired product (140 mg). API-MS: 492, 494 (M+1). $^1$H NMR (300 MHz, CDCl$_3$): d 7.8 (d, 1 H), 7.4 (t, 1 H), 7.2 (d, 1 H), 4.5 (s, 2 H), 5.15 (t, 2 H), 4.0 (s, 3 H), 2.6 (m), 1.8–1.0 (m), 1.4 (s, 9 H).

Step B: Preparation of 4-{3-[8-methoxy-2-(5-methyl-[1,3,4]thiadiazol-2-ylsulfanylmethyl)-4-oxo-4H-quinazolin-3-yl]-propyl}-piperidin-1-carboxylic acid tert-butyl ester

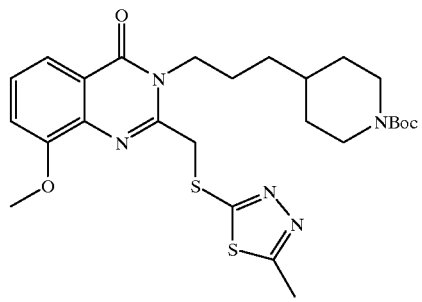

A mixture of the product from Step A (137 mg, 0.28 mmol), 2-mercapto-5-methyl-1,3,4-thiadiazole (37 mg, 0.28 mmol), and potassium carbonate (77 mg, 0.56 mmol) in DMF (15 mL) was stirred at 50° C. for 17 h. The reaction mixture was cooled to room temperature and diluted with EtOAc. The organic solution was washed with sat'd aq NaHCO$_3$, sat'd aq NaCl, dried and concentrated. The crude residue was purified using SiO$_2$-gel chromatography using 50% EtOAc/hexanes to yield the desired product as a yellow solid. API-MS: 546 (M+1). $^1$H NMR (300 MHz, CDCl$_3$): d 7.8 (d, 1 H), 7.4 (t, 1 H), 7.2 (d, 1 H), 4.95 (s, 2 H), 4.1 (t, 2 H), 4.0 (s, 3 H), 2.75 (s, 3 H), 2.8 (t, 3 H), 1.8–1.0 (m), 1.45 (s, 9 H).

Step C: Preparation of 8-methoxy-2-(5-methyl-[1,3,4]thiadiazol-2-ylsulfanylmethyl)-3-(3-piperidin-4-yl-propyl)-3H-quinazolin-4-one hydrochloride

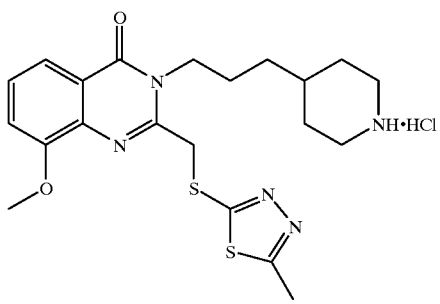

A solution of the product from Step C (35 mg) in conc HCl/EtOH (1:1 mixture, 1 mL) was stirred at room temperature for 2 h. The reaction mixture was concentrated in vacuo and azeotroped with EtOH (3×) to yield the desired product as a colorless solid. API-MS: 446 (M+1). $^1$H NMR (300 MHz, d6-MeOH): d 7.85 (d, 1 H), 7.65 (t, 1 H), 7.58 (d, 1 H), 4.9 (s), 4.3 (t, 2 H), 4.1 (s, 3 H), 3.65 (m), 3.4 (m), 3.0 (m), 2.0–1.2 (m).

Example 7

2-[2-(4-Chloro-phenyl)-vinyl]-3-[3-(1-phenethyl-piperidin-4-yl)-propyl]-8-(3-piperidin-1-yl-propoxy)-3H-quinazolin-4-one Step A: Preparation of 2-[2-(4-chloro-phenyl)-vinyl]-8-hydroxy-3-[3-(1-phenethyl-piperidin-4-yl)-propyl]-3H-quinazolin-4-one

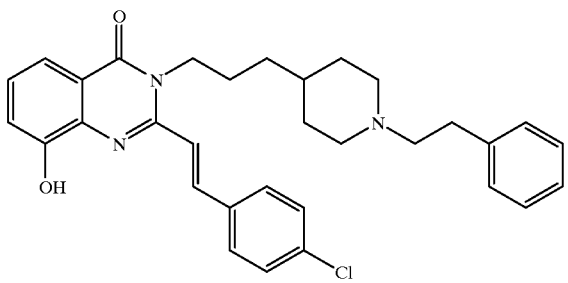

A solution of 2-[2-(4-chloro-phenyl)-vinyl]-8-methoxy-3-[3-(1-phenethyl-piperidin-4-yl)-propyl]-3H-quinazolin-4-one (530 mg, 0.98 mmol) in conc HBr/HOAc (1:1 mixture, 60 mL) was heated at 120° C. for 48 h. After cooling to room temperature, the reaction mixture was concentrated under vacuum to yield the desired product. API-MS: 529 (M+1)

Step B: Preparation of 2-[2-(4-chloro-phenyl)-vinyl]-3-[3-(1-phenethyl-piperidin-4-yl)-propyl]-8-(3-piperidin-1-yl-propoxy)-3H-quinazolin-4-one

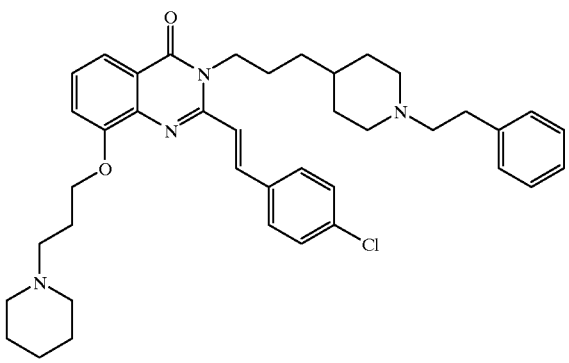

A mixture of the product from Step A (50 mg, 0.095 mmol) and sodium hydride (4.3 mg, 0.11 mmol) in DMF (1 mL) was heated at 50 C for 0.5 h, then a mixture of N-(3-chloropropyl)-piperidine hydrochloride (18 mg, 0.11 mmol) and sodium iodide (3 mg, 0.02 mmol) in DMF (1 mL) was added. The reaction mixture was heated at 80° C. for 17 h, cooled to room temperature and diluted with EtOAc. The organic solution was washed with sat'd aq NaHCO$_3$, sat'd aq NaCl, dried and concentrated. The crude residue chromatographed using 10% NEt$_3$/EtOAc to provide the desired product as a light yellow oil. AP-MS: 654 (M+1).

Example 8

(6,7-Dimethoxy-3-styryl-quinoxalin-2-yl)-[3-(1-phenethyl-piperidin-4-yl)-propyl]-amine Step A: 4-[3-(6,7-dimethoxy-3-styryl-quinoxalin-2-ylamino)-propyl]-piperidine-1-carboxylic acid tert-butyl ester

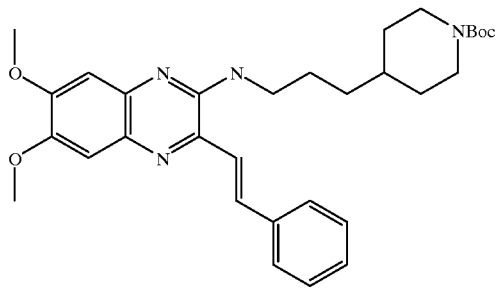

A mixture 2-chloro-6,7-dimethoxy-3-styryl-quinoxaline (see Kadin, S. B., Ger Offen., DE 2357186; 255 mg, 0.78 mmol), 4-(3-amino-propyl)-piperidine-1-carboxylic acid tert-butyl ester (see Egbertson, M, U.S. Pat. No. 5494921; 392 mg, 1.6 mmol) and potassium carbonate (220 mg, 1.6 mmol) was heated at 120° C. in DMSO (2 mL) for 17 h. After cooling to room temperature, the reaction mixture was diluted with EtOAc and washed with sat'd aq NaHCO$_3$, sat'd aq NaCl, dried and concentrated under vacuum. The crude residue was chromatographed on SiO$_2$-gel to give 150 mg of a yellow oil. API-MS: 533 (M+1). $^1$H NMR (300 MHz, CDCl$_3$): d 7.75 (d, 1 H), 7.58 (d, 1 H), 7.35 (m), 7.15 (d, 1 H), 4.05 (m), 3.99 (s, 3 H), 3.97 (s, 3 H), 3.54 (bs, 1 H), 2.68 (t, 2 H), 1.75 (m), 1.42 (s, 9 H), 1.1 (m).

Step B: (6,7-dimethoxy-3-styryl-quinoxalin-2-yl)-(3-piperidin-4-yl-propyl)-amine hydrochloride

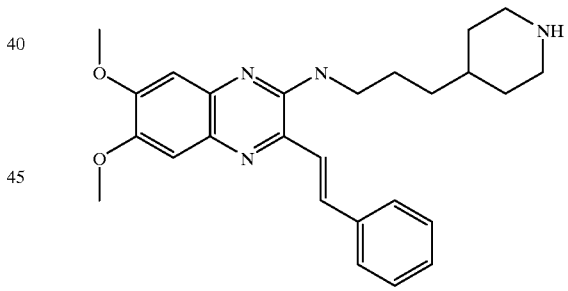

A solution of the product from Step A above (150 mg, 0.28 mmol) in conc HCl/EtOH (1:2 mixture, 3 mL) was stirred for 2 h at room temperature. The reaction mixture was concentrated under vacuum and the residue was azeotroped twice with ethanol to give the desired product as an amorphous solid. API-MS: 433 (M+1). $^1$H NMR (300 MHz, d$_4$-MeOH): d 8.0 (d, 2 H), 7.75 (d, 2 HO, 7.66 (d, 2 H), 7.4 (m), 4.0 (s, 3 H), 3.96 (s, 3 H)m 3.65 (t, 2 H), 3.28 (m, 2 H), 2.96 (t, 2 H), 2.0–1.2 (m).

Step C: (6,7-dimethoxy-3-styryl-quinoxalin-2-yl)-[3-(1-phenethyl-piperidin-4-yl)-propyl-]amine

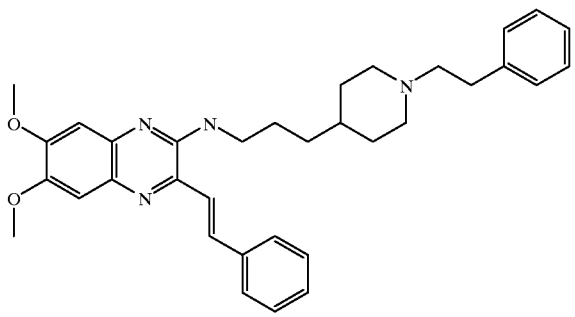

A mixture of the product from Step B above (28 mg, 0.06 mmol), 2-iodoethylbenzene (26 mg, 0.016 ml, 0.11 mmol) and potassium carbonate (15 mg, 0.11 mmol) was heated in DMF at 80° C. for 17 h. The reaction mixture was cooled to room temperature and diluted with EtOAc. The organic solution was washed with sat'd aq NaHCO$_3$, sat'd aq NaCl, dried and concentrated under vacuum. The crude residue was chromatographed on SiO$_2$-gel using a gradient of 75% ethyl acetate/hexanes to 100% ethyl acetate to yield the desired product. API-MS: 537 (M+1). $^1$H NMR (300 MHz, CDCl$_3$): d 7.77 (d,1 H), 7.61 (t,1 H), 7.4–7.15 (m), 4.02 (s, 3 H), 3.99 (s, 3 H), 3.6 (t, 4 H), 3.24 (m, 2 H), 3.12 (, 2 H), 2.6 (q, 2 H), 2.10 (m, 2 H), 1.9 (m, 2 H), 1.76 (m, 2 H).

The following compounds were prepared by the methods described in Example 8:

TABLE 6

| Ex | —NHR | MS Method: M + 1 |
|---|---|---|
| 8a | 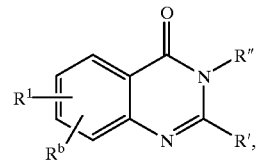 | API-MS: 351 |
| 8b | 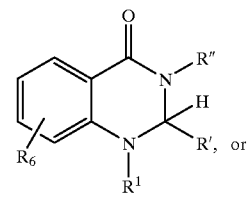 | API-MS: 419 |
| 8c | 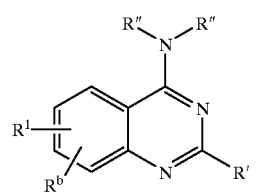 | API-MS: 545 |

TABLE 6-continued

| Ex | —NHR | MS Method: M + 1 |
|---|---|---|
| 8d | 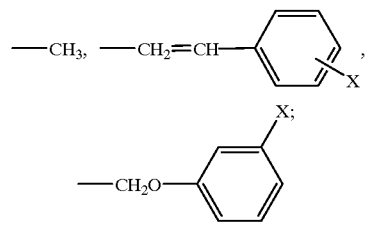 | API-MS: 545 |

What is claimed is:

1. A compound of the formula wherein:

R$^1$ is selected from —CH$_3$, —CH$_2$X, —OCH$_3$, halogen;

R$^b$ is H;

R′ is selected from

—CH$_3$, —CH$_2$=CH—⟨phenyl-X⟩,

—CH$_2$O—⟨phenyl-X⟩;

R" is selected from

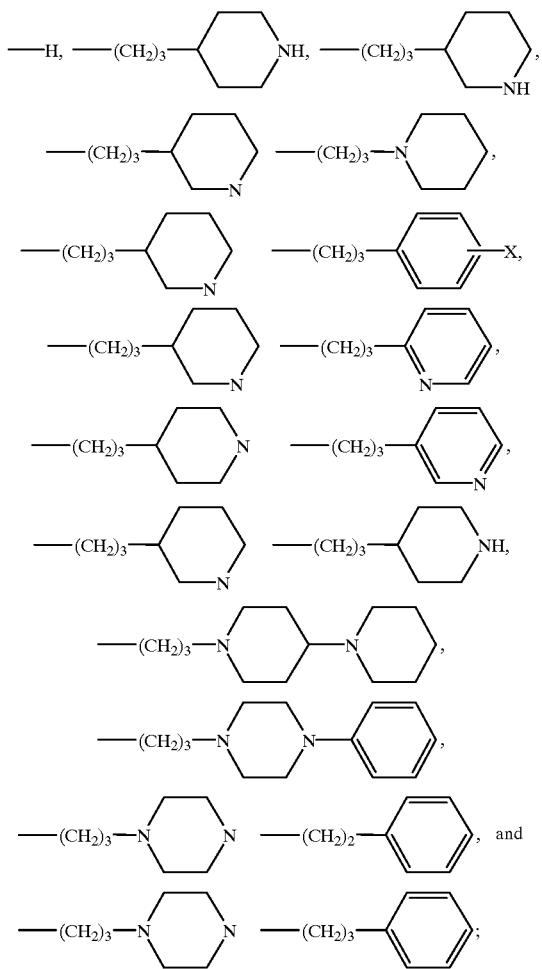

wherein X is F, Cl or Br; proviso that R" is not H in formulae I & II, and that one of any R" is not H in formulae V.

2. A compound of formula I of claim 1, wherein $R^1$ is —$CH_3$ or —$OCH_3$;

$R^b$ is H;

R' is

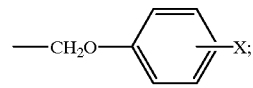

R" is

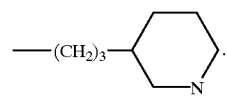

3. A compound of claim 1 which is:
2-(4-Chloro-phenoxymethyl)-8-methoxy-3H-quiniazoline-4-one;
2-(4-Chloro-phenoxymethyl)-8-methoxy-3-(3-piperidin-4-yl-propyl)-3H-quinazolin-4-one hydroclhloride;
2-(4-Chloro-phenoxymethyl)-8-methoxy-3-{3-[1-(3-piperidin-1-yl-propyl)-piperidin-4-yl]-propyl}-3H-quinazolin-4-one;
3-(3-[1,4']Bipiperidinyl-1'-yl-propyl)-2-(4-chloro-phenoxymethyl)-8-methoxy-3H-quinazolin-4-one dihydrochlroride;
2-[2-(4-Chloro-phenyl)-vinyl]-8-methoxy-3-{3-[1-(3-piperidin-1-yl-propyl)-piperidin-4-yl]-propyl}-3H-quinazolin-4-one;
8-Methoxy-2-(5-methyl-[1,3,4]thiadiazol-2-ylsulfanylmethyl)-3-(3-piperidin-4-yl-propyl)-3H-quinazolin-4-one; or
2-[2-(4-Chloro-phenyl)-vinyl]-3-[3-(1-phenethyl-piperidin-4-yl)-propyl]-8-(3-piperidin-1-yl-propoxy)-3H-quinazolin-4-one.

4. A pharmaceutical formulation, comprising, as an active ingredient, a compound of claim 1 in combination with one or more pharmaceutically acceptable carriers, diluents, or excipients, therefor.

* * * * *